United States Patent
Ogle et al.

(10) Patent No.: US 10,716,915 B2
(45) Date of Patent: Jul. 21, 2020

(54) CATHETER SYSTEMS FOR APPLYING EFFECTIVE SUCTION IN REMOTE VESSELS AND THROMBECTOMY PROCEDURES FACILITATED BY CATHETER SYSTEMS

(71) Applicant: MIVI Neuroscience, Inc., Eden Prairie, MN (US)

(72) Inventors: Matthew Ogle, Edina, MN (US); James Alexander, Excelsior, MN (US); Alexander Halaszyn, St. Paul, MN (US)

(73) Assignee: MIVI Neuroscience, Inc., Eden Prairie, MN (US)

( * ) Notice: Subject to any disclaimer, the term of this patent is extended or adjusted under 35 U.S.C. 154(b) by 633 days.

(21) Appl. No.: 14/949,574

(22) Filed: Nov. 23, 2015

(65) Prior Publication Data

US 2017/0143938 A1 May 25, 2017

(51) Int. Cl.
*A61B 17/22* (2006.01)
*A61M 25/00* (2006.01)
(Continued)

(52) U.S. Cl.
CPC ......... *A61M 25/0074* (2013.01); *A61B 17/22* (2013.01); *A61M 1/008* (2013.01);
(Continued)

(58) Field of Classification Search
CPC ......... A61B 17/22; A61B 2017/22079; A61M 1/008
See application file for complete search history.

(56) References Cited

U.S. PATENT DOCUMENTS 2,730,101 A  1/1956 Hoffman
3,949,757 A  4/1976 Sabel
(Continued)

FOREIGN PATENT DOCUMENTS

EP  0117940 A2  9/1984
EP  1226795 A2  7/2002
(Continued)

OTHER PUBLICATIONS

Feldman, "Transcatheter Aspiration of a Thrombus in an Aortocoronary Saphenous Vein Graft," American Journal of Cardiology, 60(4):379-380 ( 1987).
Penumbra, Inc., "Penumbra, Inc. Completes Pivotal Stroke Trial of Intracranial Revascularization" Press Release (2007).
Penumbra, Inc., "The Penumbra Pivotal Stroke Trial: Safety and Effectiveness of a New Generation of Mechanical Devices for Clot Removal in Intracranial Large Vessel Occlusive Disease," Stroke 2009, 40:2761-2768.
(Continued)

*Primary Examiner* — Julie A Szpira
(74) *Attorney, Agent, or Firm* — Christensen, Fonder, Dardi & Herbert PLLC; Peter S. Dardi

(57) ABSTRACT

A suction catheter system is described with a suction nozzle that can extend from a guide catheter of the like. The suction nozzle can be positioned by tracking the suction nozzle through a vessel while moving a proximal portion of the suction extension within the lumen of the guide catheter. A suction lumen extends from the proximal end of the guide catheter through at least part of the guide catheter central lumen and through the suction tip. Desirable suction flow can be established using the guide lumen to facilitate the suction. Also, a delivery catheter is described with an elastic tip that can track closely over a guidewire. The elastic tip of the delivery catheter can be expanded to provide for the delivery of medical devices past the tip.

23 Claims, 13 Drawing Sheets

(51) Int. Cl.
*A61M 1/00* (2006.01)
*A61M 25/09* (2006.01)
*A61M 25/10* (2013.01)
*A61B 17/221* (2006.01)
*A61M 25/01* (2006.01)
*A61B 17/00* (2006.01)

(52) U.S. Cl.
CPC ............ *A61M 25/09* (2013.01); *A61M 25/10* (2013.01); *A61B 17/22032* (2013.01); *A61B 2017/00991* (2013.01); *A61B 2017/2212* (2013.01); *A61B 2017/22079* (2013.01); *A61B 2217/005* (2013.01); *A61M 25/0068* (2013.01); *A61M 2025/0004* (2013.01); *A61M 2025/0006* (2013.01); *A61M 2025/0175* (2013.01)

(56) References Cited

U.S. PATENT DOCUMENTS

| | | |
|---|---|---|
| 3,996,938 A | 12/1976 | Clark, III |
| 4,020,829 A | 5/1977 | Wilson et al. |
| 4,033,331 A | 7/1977 | Guss et al. |
| 4,174,715 A | 11/1979 | Hasson |
| 4,610,662 A | 9/1986 | Welkl et al. |
| 4,619,263 A | 10/1986 | Frisbie et al. |
| 4,676,249 A | 6/1987 | Arenas et al. |
| 4,723,549 A | 2/1988 | Wholey et al. |
| 4,728,319 A | 3/1988 | Masch |
| 4,739,768 A | 4/1988 | Engleson |
| 4,784,636 A | 11/1988 | Rydell |
| 4,790,812 A | 12/1988 | Hawkins, Jr. et al. |
| 4,794,928 A | 1/1989 | Kletschka |
| 4,795,434 A | 1/1989 | Kujawski |
| 4,799,496 A | 1/1989 | Hargreaves et al. |
| 4,834,709 A | 5/1989 | Banning et al. |
| 4,863,431 A | 9/1989 | Vaillancourt |
| 4,873,978 A | 10/1989 | Ginsburg |
| 4,873,979 A | 10/1989 | Ginsburg |
| 4,883,460 A | 11/1989 | Zanetti |
| 4,887,613 A | 12/1989 | Farr et al. |
| 4,900,303 A | 2/1990 | Lemelson |
| 4,921,484 A | 5/1990 | Hillstead |
| 4,994,067 A | 2/1991 | Summers |
| 4,998,919 A | 3/1991 | Schnepp-Pesch et al. |
| 5,011,488 A | 4/1991 | Ginsburg |
| 5,011,490 A | 4/1991 | Fischell et al. |
| 5,053,008 A | 10/1991 | Bajaj |
| 5,059,178 A | 10/1991 | Ya |
| 5,102,415 A | 4/1992 | Guenther et al. |
| 5,108,419 A | 4/1992 | Reger et al. |
| 5,152,277 A | 10/1992 | Honda et al. |
| 5,161,534 A | 11/1992 | Berthaume |
| 5,163,906 A | 11/1992 | Ahmadi |
| 5,185,004 A | 2/1993 | Lashinski |
| 5,188,621 A | 2/1993 | Samson |
| 5,200,248 A | 4/1993 | Thompson et al. |
| 5,211,651 A | 5/1993 | Reger et al. |
| 5,219,332 A | 6/1993 | Nelson et al. |
| 5,308,318 A | 5/1994 | Plassche, Jr. |
| 5,312,338 A | 5/1994 | Nelson et al. |
| 5,325,868 A | 7/1994 | Kimmelstiel |
| 5,352,197 A | 10/1994 | Hammersmark et al. |
| 5,364,358 A * | 11/1994 | Hewitt ................ A61M 16/044 604/99.01 |
| 5,392,778 A | 2/1995 | Horzewski |
| 5,395,383 A | 3/1995 | Adams et al. |
| 5,409,859 A | 4/1995 | Glass et al. |
| 5,413,575 A * | 5/1995 | Haenggi ............ A61B 18/1402 606/39 |
| 5,423,331 A | 6/1995 | Wysham |
| 5,438,993 A | 8/1995 | Lynch et al. |
| 5,465,716 A | 11/1995 | Avitall |
| 5,485,667 A | 1/1996 | Kleshinski |
| 5,501,694 A | 3/1996 | Resseman et al. |
| 5,527,292 A | 6/1996 | Adams et al. |
| 5,533,967 A | 7/1996 | Irman |
| 5,546,958 A | 8/1996 | Throud et al. |
| 5,549,626 A | 8/1996 | Miller et al. |
| 5,571,122 A | 11/1996 | Kelly et al. |
| 5,578,009 A | 11/1996 | Kraus et al. |
| 5,599,307 A | 2/1997 | Bacher et al. |
| 5,720,764 A | 2/1998 | Naderlinger |
| 5,766,191 A | 6/1998 | Trerotola |
| 5,776,142 A | 7/1998 | Gunderson |
| 5,810,874 A | 9/1998 | Lefebvre |
| 5,814,064 A | 9/1998 | Daniel et al. |
| 5,817,101 A | 10/1998 | Fiedler |
| 5,836,868 A | 11/1998 | Resseman et al. |
| 5,843,002 A | 12/1998 | Pecor et al. |
| 5,843,051 A | 12/1998 | Adams et al. |
| 5,851,189 A | 12/1998 | Forber |
| 5,882,329 A | 3/1999 | Patterson et al. |
| 5,897,567 A | 4/1999 | Resseman et al. |
| 5,899,890 A | 5/1999 | Chiang et al. |
| 5,910,154 A | 6/1999 | Tsugita et al. |
| 5,911,725 A | 6/1999 | Boury |
| 5,911,734 A | 6/1999 | Tsugita et al. |
| 5,928,260 A | 7/1999 | Chin et al. |
| 5,935,139 A | 8/1999 | Bates |
| 5,938,645 A | 8/1999 | Gordon |
| 5,941,869 A | 8/1999 | Patterson et al. |
| 5,972,019 A | 10/1999 | Engleson et al. |
| 5,997,557 A | 12/1999 | Barbut et al. |
| 6,010,522 A | 1/2000 | Barbut et al. |
| 6,022,336 A | 2/2000 | Zando-Azizi et al. |
| 6,030,349 A | 2/2000 | Wilson et al. |
| 6,030,369 A | 2/2000 | Engleson et al. |
| 6,066,149 A | 5/2000 | Samson et al. |
| 6,106,530 A | 8/2000 | Harada |
| 6,117,141 A | 9/2000 | Ouchi |
| 6,135,991 A | 10/2000 | Muni et al. |
| 6,142,987 A | 11/2000 | Tsugita |
| 6,146,396 A | 11/2000 | Konya et al. |
| 6,156,005 A | 12/2000 | Theron |
| 6,159,195 A | 12/2000 | Ha et al. |
| 6,159,230 A * | 12/2000 | Samuels .......... A61B 17/22031 606/200 |
| 6,168,579 B1 * | 1/2001 | Tsugita ............ A61B 17/12109 604/104 |
| 6,203,561 B1 | 3/2001 | Ramee et al. |
| 6,206,868 B1 | 3/2001 | Parodi |
| 6,221,049 B1 | 4/2001 | Selmon et al. |
| 6,238,402 B1 | 5/2001 | Sullivan, III et al. |
| 6,238,412 B1 | 5/2001 | Dubrul et al. |
| 6,240,231 B1 | 5/2001 | Ferrera et al. |
| 6,258,115 B1 | 7/2001 | Dubrul |
| 6,270,477 B1 | 8/2001 | Bagaosian et al. |
| 6,277,139 B1 | 8/2001 | Levinson et al. |
| 6,306,163 B1 | 10/2001 | Fitz |
| 6,346,116 B1 | 2/2002 | Brooks et al. |
| 6,361,545 B1 | 3/2002 | Macoviak et al. |
| 6,364,894 B1 | 4/2002 | Healy et al. |
| 6,368,338 B1 | 4/2002 | Konya et al. |
| 6,391,044 B1 | 5/2002 | Yadav et al. |
| 6,454,741 B1 | 9/2002 | Muni et al. |
| 6,454,775 B1 | 9/2002 | Demarais et al. |
| 6,485,466 B2 | 11/2002 | Hamilton |
| 6,485,500 B1 | 11/2002 | Kokish et al. |
| 6,485,501 B1 | 11/2002 | Green |
| 6,511,470 B1 | 1/2003 | Hamilton |
| 6,511,471 B2 | 1/2003 | Rosenman et al. |
| 6,514,261 B1 | 2/2003 | Randall et al. |
| 6,514,273 B1 | 2/2003 | Voss et al. |
| 6,537,295 B2 | 3/2003 | Petersen |
| 6,540,768 B1 | 4/2003 | Diaz et al. |
| 6,551,302 B1 | 4/2003 | Rosinko et al. |
| 6,558,405 B1 | 5/2003 | McInnes |
| 6,569,148 B2 | 5/2003 | Bagaosian et al. |
| 6,579,484 B1 | 6/2003 | Tiernan et al. |
| 6,589,262 B1 | 7/2003 | Honebrink et al. |
| 6,596,011 B2 | 7/2003 | Johnson et al. |
| 6,610,077 B1 | 8/2003 | Hancock et al. |
| 6,616,681 B2 | 9/2003 | Hanson et al. |

(56) References Cited

U.S. PATENT DOCUMENTS

| | | | |
|---|---|---|---|
| 6,620,148 B1 | 9/2003 | Tsugita | |
| 6,695,858 B1 * | 2/2004 | Dubrul | A61B 17/221 606/159 |
| 6,695,865 B2 | 2/2004 | Boyle et al. | |
| 6,702,834 B1 | 3/2004 | Boylan et al. | |
| 6,773,448 B2 | 8/2004 | Kusleika et al. | |
| 6,787,151 B2 | 9/2004 | Meijer et al. | |
| 6,805,684 B2 | 10/2004 | Bonnette et al. | |
| 6,805,692 B2 | 10/2004 | Muni et al. | |
| 6,824,553 B1 | 11/2004 | Samson et al. | |
| 6,866,669 B2 | 3/2005 | Buzzard et al. | |
| 6,879,854 B2 | 4/2005 | Windheuser et al. | |
| 6,911,036 B2 | 6/2005 | Douk et al. | |
| 6,945,956 B2 | 9/2005 | Waldhauser et al. | |
| 6,949,104 B2 | 9/2005 | Griffis et al. | |
| 6,951,570 B2 | 10/2005 | Linder et al. | |
| 6,958,059 B2 | 10/2005 | Zando-Azizi | |
| 6,969,395 B2 | 11/2005 | Eskuri et al. | |
| 6,991,642 B2 | 1/2006 | Petersen | |
| 7,052,500 B2 | 5/2006 | Bashiri et al. | |
| 7,056,328 B2 | 6/2006 | Arnott | |
| 7,115,134 B2 | 10/2006 | Chambers | |
| 7,115,138 B2 | 10/2006 | Renati et al. | |
| 7,166,120 B2 | 1/2007 | Kusleika | |
| 7,220,271 B2 | 5/2007 | Clubb et al. | |
| 7,229,431 B2 | 6/2007 | Houser et al. | |
| 7,229,463 B2 | 6/2007 | Sutton et al. | |
| 7,229,464 B2 | 6/2007 | Hanson et al. | |
| 7,232,452 B2 | 6/2007 | Adams et al. | |
| 7,285,126 B2 * | 10/2007 | Sepetka | A61B 17/22031 606/113 |
| 7,309,334 B2 | 12/2007 | von Hoffman | |
| 7,329,278 B2 | 2/2008 | Seguin et al. | |
| 7,374,564 B2 * | 5/2008 | Brown | A61B 17/221 606/113 |
| 7,449,010 B1 * | 11/2008 | Hayase | A61M 25/0054 604/93.01 |
| 7,476,232 B2 * | 1/2009 | Deal | A61M 25/04 606/127 |
| 7,549,974 B2 | 6/2009 | Nayak | |
| 7,625,207 B2 * | 12/2009 | Hershey | A61C 1/16 433/100 |
| 7,736,355 B2 | 6/2010 | Itou et al. | |
| 7,842,055 B2 | 11/2010 | Pintor et al. | |
| 7,879,062 B2 | 2/2011 | Galdonik et al. | |
| 7,938,820 B2 | 5/2011 | Webster et al. | |
| 8,021,351 B2 | 9/2011 | Boldenow et al. | |
| 8,048,032 B2 | 11/2011 | Root et al. | |
| 8,092,483 B2 | 1/2012 | Galdonik et al. | |
| 8,231,600 B2 | 7/2012 | von Hoffman | |
| 8,308,712 B2 | 11/2012 | Provost et al. | |
| 8,419,786 B2 | 4/2013 | Cottone, Jr. et al. | |
| 8,465,456 B2 * | 6/2013 | Stivland | A61B 17/22 604/103.04 |
| 8,764,813 B2 | 7/2014 | Jantzen et al. | |
| 8,795,305 B2 | 8/2014 | Martin et al. | |
| 8,814,892 B2 | 8/2014 | Galdonik et al. | |
| 8,932,286 B2 * | 1/2015 | Terry | A61B 18/1402 606/27 |
| 9,199,057 B2 * | 12/2015 | Nielsen | A61M 25/002 |
| 9,433,427 B2 * | 9/2016 | Look | A61B 17/22 |
| 9,561,345 B2 | 2/2017 | Garrison et al. | |
| 9,993,613 B2 * | 6/2018 | Wang | A61M 25/01 |
| 10,213,582 B2 * | 2/2019 | Garrison | A61M 25/0054 |
| 2001/0031980 A1 | 10/2001 | Wensel | A61B 17/221 606/200 |
| 2001/0044600 A1 * | 11/2001 | Elkins | A61M 16/0463 604/119 |
| 2001/0044632 A1 | 11/2001 | Daniel et al. | |
| 2001/0051811 A1 | 12/2001 | Bonnette et al. | |
| 2002/0035347 A1 | 3/2002 | Bagaoisan et al. | |
| 2002/0055747 A1 | 5/2002 | Cano et al. | |
| 2002/0062133 A1 | 5/2002 | Gilson et al. | |
| 2002/0095174 A1 | 7/2002 | Tsugita et al. | |
| 2002/0111648 A1 | 8/2002 | Kusleika et al. | |
| 2002/0123765 A1 * | 9/2002 | Sepetka | A61B 17/22031 606/192 |
| 2002/0133111 A1 | 9/2002 | Shadduck | |
| 2002/0143362 A1 | 10/2002 | Mackoviak et al. | |
| 2002/0151927 A1 | 10/2002 | Douk et al. | |
| 2002/0165574 A1 | 11/2002 | Ressemann et al. | |
| 2002/0169472 A1 | 11/2002 | Douk et al. | |
| 2002/0183782 A1 | 12/2002 | Tsugita et al. | |
| 2003/0023263 A1 | 1/2003 | Krolik et al. | |
| 2003/0065353 A1 | 4/2003 | Horzewski et al. | |
| 2003/0120208 A1 | 6/2003 | Houser et al. | |
| 2003/0135232 A1 | 7/2003 | Douk et al. | |
| 2003/0191492 A1 * | 10/2003 | Gellman | A61B 17/221 606/200 |
| 2004/0006344 A1 | 1/2004 | Nguyen et al. | |
| 2004/0006365 A1 | 1/2004 | Brady et al. | |
| 2004/0015151 A1 | 1/2004 | Chambers | |
| 2004/0153118 A1 | 8/2004 | Clubb et al. | |
| 2004/0220611 A1 | 11/2004 | Ogle | |
| 2004/0254602 A1 | 12/2004 | Lehe et al. | |
| 2005/0004553 A1 | 1/2005 | Douk | |
| 2005/0021075 A1 | 1/2005 | Bonnette et al. | |
| 2005/0021152 A1 | 1/2005 | Ogle et al. | |
| 2005/0075661 A1 | 4/2005 | Levine et al. | |
| 2005/0085847 A1 | 4/2005 | Galdonik et al. | |
| 2005/0209631 A1 | 9/2005 | Galdonik et al. | |
| 2005/0228479 A1 | 10/2005 | Pavcnik et al. | |
| 2005/0277976 A1 | 12/2005 | Galdonik et al. | |
| 2006/0030876 A1 | 2/2006 | Peacock, III et al. | |
| 2006/0047301 A1 | 3/2006 | Ogle | |
| 2006/0129091 A1 | 6/2006 | Bonnette et al. | |
| 2006/0195137 A1 * | 8/2006 | Sepetka | A61B 17/22 606/200 |
| 2006/0200047 A1 | 9/2006 | Galdonik et al. | |
| 2006/0200191 A1 | 9/2006 | Zando-Azizi | |
| 2007/0060908 A1 | 3/2007 | Webster et al. | |
| 2007/0060911 A1 | 3/2007 | Webster et al. | |
| 2007/0060944 A1 | 3/2007 | Boldenow et al. | |
| 2007/0135733 A1 | 6/2007 | Soukup et al. | |
| 2007/0135832 A1 | 6/2007 | Wholey | |
| 2007/0185501 A1 * | 8/2007 | Martin | A61B 17/22012 606/114 |
| 2007/0197956 A1 | 8/2007 | Le et al. | |
| 2007/0227543 A1 * | 10/2007 | Peichel | A61M 25/00 128/207.14 |
| 2007/0250040 A1 | 10/2007 | Provost et al. | |
| 2007/0250096 A1 | 10/2007 | Yamane et al. | |
| 2007/0260115 A1 | 11/2007 | Brock et al. | |
| 2008/0086110 A1 * | 4/2008 | Galdonik | A61M 25/00 604/509 |
| 2008/0109088 A1 | 5/2008 | Galdonik et al. | |
| 2008/0172066 A9 | 7/2008 | Galdonik et al. | |
| 2009/0076319 A1 | 3/2009 | Muyari | |
| 2009/0131970 A1 | 5/2009 | Chanduszko et al. | |
| 2010/0204672 A1 | 8/2010 | Lockhart et al. | |
| 2010/0211050 A1 * | 8/2010 | Luther | A61M 25/0017 604/544 |
| 2011/0093000 A1 | 4/2011 | Ogle et al. | |
| 2011/0172678 A1 * | 7/2011 | Behl | A61M 25/0102 606/127 |
| 2012/0123466 A1 | 5/2012 | Porter et al. | |
| 2012/0253313 A1 | 10/2012 | Galdonik et al. | |
| 2013/0184742 A1 | 7/2013 | Ganesan et al. | |
| 2014/0018773 A1 | 1/2014 | Wang et al. | |
| 2014/0117397 A1 | 5/2014 | Saeki et al. | |
| 2014/0249508 A1 | 9/2014 | Wang et al. | |
| 2015/0173782 A1 | 6/2015 | Garrison et al. | |
| 2015/0282821 A1 * | 10/2015 | Look | A61B 17/22 606/127 |
| 2015/0327919 A1 * | 11/2015 | Clopp | A61B 18/1485 606/41 |
| 2016/0066931 A1 * | 3/2016 | Kugler | A61B 17/22031 606/127 |
| 2016/0166754 A1 | 6/2016 | Kassab et al. | |
| 2016/0199620 A1 | 7/2016 | Pokorney et al. | |
| 2016/0220741 A1 | 8/2016 | Garrison et al. | |
| 2017/0056061 A1 | 3/2017 | Ogle et al. | |

(56) References Cited

U.S. PATENT DOCUMENTS

| | | | |
|---|---|---|---|
| 2017/0181760 A1 | 6/2017 | Look et al. | |
| 2017/0231647 A1* | 8/2017 | Saunders | A61B 17/32056 606/113 |
| 2017/0252051 A1 | 9/2017 | Wan et al. | |
| 2017/0252057 A1 | 9/2017 | Bonnette et al. | |
| 2017/0303942 A1 | 10/2017 | Greenhalgh et al. | |
| 2017/0303948 A1 | 10/2017 | Wallace et al. | |
| 2017/0333060 A1* | 11/2017 | Panian | A61B 17/22 |
| 2017/0333237 A1 | 11/2017 | Walzman | |
| 2017/0354427 A1 | 12/2017 | Bonnette et al. | |

FOREIGN PATENT DOCUMENTS

| | | |
|---|---|---|
| GB | 2020557 A | 11/1979 |
| WO | 95/05209 A1 | 2/1995 |
| WO | 98/38930 A1 | 9/1998 |
| WO | 00/16705 A1 | 3/2000 |
| WO | 02/055146 A1 | 7/2002 |
| WO | 02/085092 A2 | 10/2002 |
| WO | 2010-014777 A1 | 2/2010 |

OTHER PUBLICATIONS

Penumbra, Inc., "The Penumbra System®: Continuous Aspiration Thrombectomy (CAT)," Marketing Brochure © 2010 (6 pages).

Penumbra, Inc., "5Max™: Direct Aspiration™ Enables Choice," Marketing brochure © 2013 (6 pages).

Reeder et al., "Aspiration Thrombectomy for Removal of Coronary Thrombosis," American Journal of Cardiology, (Jul. 1, 1992) 70:107-110 (Abstract only).

Webb et al., "Retrieval and Analysis of Particulate Debris After Saphenous Vein Graft Intervention," Journal of the American College of Cardiology, 34(2);468-475 (1999).

Yoo et al., "The Penumbra Stroke System: a technical review," Journal of NeuroInterventional Surgery, 4:199-205 (2012).

Abstracts from the 2007 International Stroke Conference, 38 Stroke 453-607 (2007).

International Search Report and Written Opinion from co-pending application, PCT/US2016/063269, dated Apr. 3, 2017 (13 pages).

Communication from co-pending European Application No. 16869159.0 for PCT/US2016/063269 dated Jul. 5, 2019.

* cited by examiner

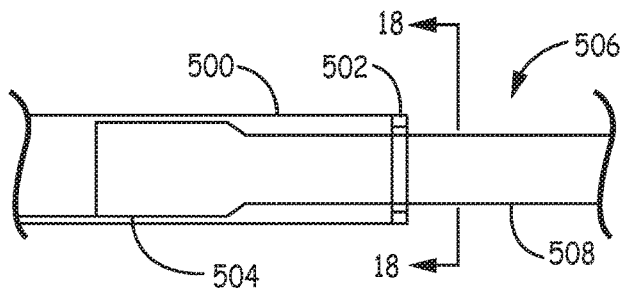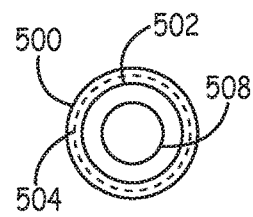
FIG. 17   FIG. 18
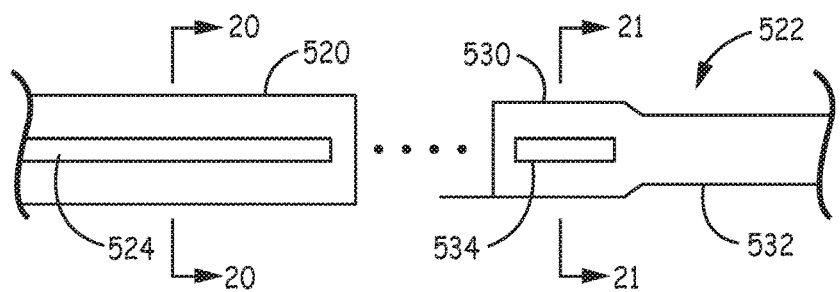
FIG. 19
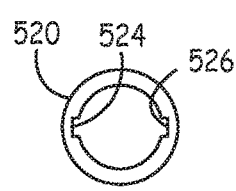 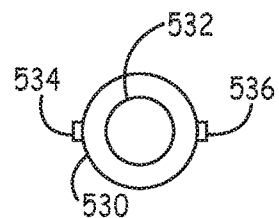
FIG. 20   FIG. 21
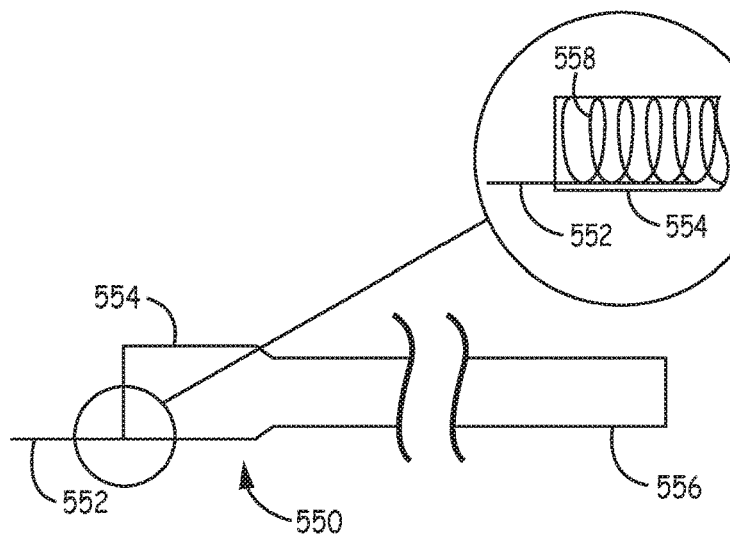
FIG. 22

CATHETER SYSTEMS FOR APPLYING EFFECTIVE SUCTION IN REMOTE VESSELS AND THROMBECTOMY PROCEDURES FACILITATED BY CATHETER SYSTEMS

FIELD OF THE INVENTION

The invention relates to catheters designed for use in bodily vessels with tortuous paths, such as cerebral arteries. The invention further relates to methods of using such catheters.

BACKGROUND OF THE INVENTION

Procedures in blood vessels of the brain are gaining interest as an approach for ameliorating acute stroke events or other interventions in blood vessels in the brain. Blood vessels in the brain follow particularly tortuous paths which can increase the difficulty of reaching target locations in these vessels. Other vessels in a patient can also follow winding paths that increase the difficulty of reaching target locations.

Aspiration catheters have found use with respect to removal of clots from vessels. Furthermore, a significant reason for ischemic injury during percutaneous procedures can be generation of emboli that block smaller distal vessels. Aspiration catheters used alone or with embolic protection device can be effective to capture emboli generated during procedures. The delivery of effective devices to the small blood vessels of the brain to remove clots and/or to capture emboli remains challenging.

Ischemic strokes can be caused by clots within a cerebral artery. The clots block blood flow, and the blocked blood flow can deprive brain tissue of its blood supply. The clots can be thrombus that forms locally or an embolus that migrated from another location to the place of vessel obstruction. To reduce the effects of the cut off in blood supply to the tissue, time is an important factor. In particular, it is desirable to restore blood flow in as short of a period of time as possible. The cerebral artery system is a highly branched system of blood vessels connected to the interior carotid arteries. The cerebral arteries are also very circuitous. Medical treatment devices should be able to navigate along the circuitous route posed by the cerebral arteries for placement into the cerebral arteries.

SUMMARY OF THE INVENTION

In a first aspect, the invention pertains to a suction catheter system comprising a guide catheter and a suction extension. The guide catheter can comprise a tubular shaft with a central lumen having an inner diameter, a proximal end and a distal opening, and a proximal section operably connected with the proximal end of the tubular shaft and having fittings that connect to a suction device. The suction extension can comprise a proximal portion, a suction tip comprising a distal opening and extending from the proximal portion in a distal direction, and a control structure connecting the proximal portion with the proximal section of the guide catheter. In some embodiments, the suction tip can have a distal inner diameter that is from about 20 percent to about 90 percent of the central lumen inner diameter. Generally, the proximal portion can be configured to slide within the central lumen of the tubular shaft to change the relative position of the proximal portion within the central lumen and provide for at least a portion of the narrow diameter suction extension to extend outward from the distal opening of the tubular shaft at appropriate configurations of the proximal portion. A suction lumen is formed extending from the fitting configured to connect to the suction device through a portion of the central lumen, the proximal portion and the suction tip to a distal opening.

In a further aspect, the invention pertains to a method for using the suction catheter system described above for performing a thrombectomy procedure. In general, the method can comprise applying suction through the suction lumen of the suction catheter system positioned with the guide catheter extending into a vessel of a patient in a percutaneous configuration, to draw fluid into the distal opening of the suction tip to remove thrombus from the vessel. The suction catheter system can be particularly suitable for performing procedures in the cerebral arteries.

In another aspect, the invention pertains to a method for performing a medical procedure in a bodily vessel using a suction catheter system comprising a guide catheter and a suction extension slidably engaged with the guide catheter, the suction extension comprising a proximal portion configured to remain in a central lumen of the guide catheter and a suction tip extending in a distal direction from the proximal portion. The method can comprise tracking the suction tip to a desired location within a vessel by sliding the suction extension relative to the guide catheter.

In additional aspects, the invention pertains to a delivery catheter comprising a proximal tubular element having an outer diameter from about 1 mm to about 3 mm and a distal tubular element comprising a distal opening and extending from the distal end of the proximal tubular element wherein the distal tubular element has an initial inner diameter no more than about 1.5 mm and at least a factor of two smaller than the proximal tubular element inner diameter. The distal tubular element generally is formed from an elastic material that can stretch to at least about 1.5 times greater than the initial inner diameter.

Moreover, the invention pertains to a method based on the delivery catheter described above for placement of a first medical device into a narrow tortuous vessel of the body. In appropriate embodiments, the method can comprise: advancing the first medical device over a guidewire through the delivery catheter out through the distal opening of the distal tubular element, and the first medical device has a radial profile relative to the guidewire axis greater than the initial inner diameter of the distal tubular element.

BRIEF DESCRIPTION OF THE DRAWINGS

FIG. 17 is a fragmentary side view of a suction system having a stop mounted at the distal end of a guide catheter.

FIG. 18 is a sectional view taken along line 18-18 of FIG. 17 showing a stop at the distal opening of the guide catheter.

FIG. 19 is a fragmentary, exploded side view of showing the suction extension separated from the guide catheter, in which a projection along the proximal portion of the suction extension rides within a track within guide catheter.

FIG. 20 is a sectional view depicting the guide catheter having a channel with the section taken along lines 20-20 of FIG. 19.

FIG. 21 is a sectional view depicting the proximal portion of the suction extension along a portion having ridges with the section taken along line 21-21 of FIG. 19.

FIG. 22 is a side view of the suction extension with the expanded insert showing the attachment of a control wire to the proximal portion.

DETAILED DESCRIPTION OF THE INVENTION

Figure 1:
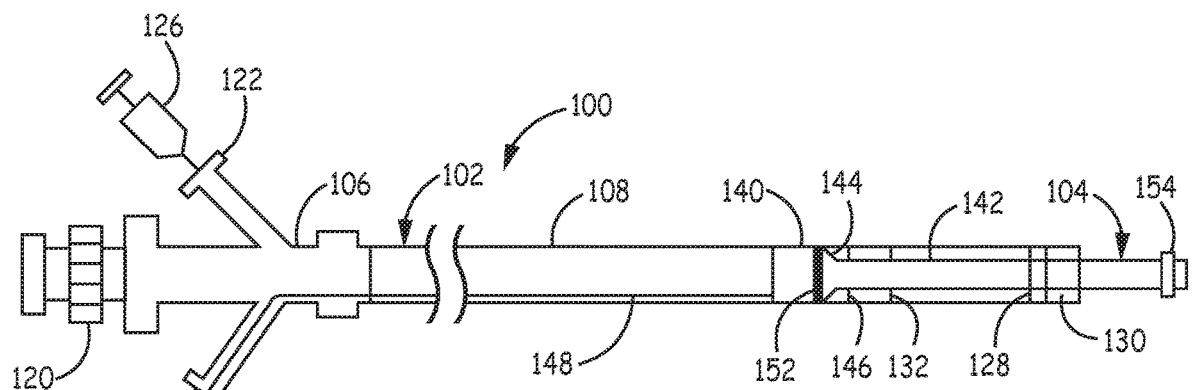
FIG. 1 is a side view of a suction system comprising a guide catheter with a suction extension with the guide catheter shown as transparent in this and most subsequent figures, as would be clear from the figure, to allow visualization of structure within the guide catheter.

A catheter system can include a guide catheter adapted with a suction extension with a narrower distal tube that can provide suction with a high flow rate and a low pressure drop. Suction catheters can be used advantageously for the removal of thrombus and emboli from bodily vessels, such as arteries. Some vessels can have a narrow diameter, and treatment locations can be downstream along a circuitous path, and for such vessels there are constraints on the catheter structures able to reach the treatment locations in the vessel. The designs described herein comprise a slidable extended suction tip that can be adapted for use in conjunction with a guide catheter, which forms a significant portion of the overall suction lumen. The slidable suction tip comprises a slide that engages the inner wall of the guide catheter to make a suitably tight fit and a control wire or other suitable control element can be attached to the suction extension to position the slidable suction tip. The extendable suction tip, which may have an optional curved tip, can be tracked well over a guidewire to reach difficult to reach locations in the vessel. While the suction catheter system can be used in any suitable vessels of the body, the system can be particularly desirable in cerebral blood vessels, such as for the treatment of acute stroke. The catheter system can be effectively used as an effective standalone suction catheter. Furthermore, the catheter system can be effective as a component of a thrombectomy treatment system or other medical system to provide suction with the use of other medical devices, such as an atherectomy device, to disrupt thrombus and/or a filter structure that can catch emboli generated in the procedure as well as to be used to pull toward the suction catheter system. The treatment system can be effectively designed for stroke treatment.

Also herein, a delivery catheter is described with an elastic narrow diameter distal tip. The narrow diameter tip can have an inner diameter just larger than a guidewire, so that the narrow tip can be effectively tracked over the guidewire to difficult to reach locations within the vasculature or other tortuous vessel. Due to the elastic nature of the tip structure, other percutaneous devices can be delivered through the delivery catheter and past the tip, which can expand significantly to accommodate passage of the device through the tip. Once other devices as desired are delivered though the delivery catheter, the delivery catheter can be removed or drawn back to a more proximal position to avoid interfering with subsequent procedures.

Less invasive procedures, which are commonly referred to in the art as minimally invasive procedures, are desirable in the medical context to reduce patient recovery times and hopefully to improve outcomes when appropriate. In particular, less invasive procedures are commonly performed in the vasculature using catheter based system for reaching remote locations in a selected blood vessel for the performance of various treatment processes. These procedures can also be referred to as percutaneous procedures or transluminal procedures, in contrast with open surgical procedures, to emphasize the delivery through a vessel lumen. The discussion herein focuses on treatment of ischemic stroke since the devices can be particularly effective to treat these clinically important conditions, although the devices can be used in other procedures both in the vasculature and other bodily vessels. Patients include humans and can include other mammals, such as pet animals and farm animals. The terms proximal and distal are used in their conventional sense in the art, i.e., proximal refers to closer to the point of entry into the patient along the path in the vasculature or other vessel and distal refers to farther from the point of entry along the path in the vasculature.

For the treatment of strokes, the treatment devices are advanced through arteries to blood vessels of the brain. Blood vessels generally relevant for acute stroke treatment are downstream in the blood flow from the internal carotid arteries, and arteries generally branch and decrease in average diameter as the vessel proceeds in a downstream direction in the arterial vasculature. The body has a right internal carotid artery and a left internal carotid artery. For convenience, the blood vessels downstream from the internal carotid arteries are referred to herein as cerebral arteries. The cerebral arteries can be accessed with catheter based systems from, for example, a femoral artery in the groin, an artery in the arm, or the carotid artery in the neck using hemostatic procedures and appropriate fittings, such as those known in the art. The cerebral arteries are known to follow circuitous paths, and complications in tracking devices along the vessels also follows due to shrinkage in diameter and branching of the vessels in a distal direction from the carotid artery as well as potentially dangerous conditions from damage to the blood vessel. It can be desirable to access tortuous narrow arteries for stroke treatment. The devices described herein are designed for advantageous use in these tortuous narrow cerebral vessels, but a person of ordinary skill in the art will recognize utility of these devices in other medical procedures.

The present suction catheter systems incorporate guide catheters adapted with a slideable suction extension suitable for cerebral procedures. In vascular procedures generally, a guide catheter can be used to facilitate the delivery of therapeutic devices while allowing for more rapid, accurate delivery with less risk to vessel walls through providing a protected channel leading most of the way to the treatment site. In the cerebral procedures, a guide catheter can be placed from exterior of the patient at the point of entry into the vasculature with the distal end of the guide catheter in the carotid artery or interior carotid artery. Thus, a guide catheter provides a lumen to a location relatively near to a treatment site. The size of the guide catheter sets limits on the diameter of treatment structures delivered to the treatment site, but this is generally not a significant issue since extendable devices can be delivered in a lower profile configuration with subsequent deployments to the extended and configuration and since the vessel sizes generally decrease in a distal direction from the guide catheter limiting the need for larger treatment devices. The suction devices described herein provide a suction extension that can protrude from the distal end of the guide catheter an adjustable amount through the positioning of a proximal portion of the suction extension interfacing the suction extension with the walls of the guide catheter. The proximal portion can make a sufficiently tight seal with the guide catheter walls such that suction in the guide catheter lumen is transmitted along the lumen of the suction extension. Desirable degrees of suction can be obtained through the suction extension using suction applied at the proximal end of the guide catheter.

The suction extension generally comprises a proximal portion and a suction tip extending in a distal direction from the proximal portion. The suction extension generally interfaces with the guide catheter and can be designed to be positioned with its tip at a selected position distal to the guide catheter for the performance of a procedure at a selected location, such as near the location of thrombus occluding a vessel. Since the relative position of the treatment location and the distal end of the guide catheter generally vary for a specific medical situation, the degree in which the suction extension extends from the guide catheter can be adjusted through relative movement of the suction extension. A control element, e.g., wire, can be secured to the suction extension to provide for the positioning of the suction extension. The suction extension should move within the guide catheter lumen without the need for excessive force, such as through the use of low friction polymers on one or both adjacent surfaces. Also, the proximal portion of the suction extension should provide for a relatively tight fit with the guide catheter inner wall so that significant amounts of fluid do not flow between the suction extension and the guide catheter wall when negative pressure is applied in the guide catheter lumen. The tight fit can be provided, for example, through a low clearance between the proximal portion of the suction extension and the catheter wall, through the use of a mechanical seal, such as an o-ring, wiper seal, expandable balloon, other suitable elastic seal or the like. Also, since it is desirable to prevent the proximal portion of the suction extension from exiting from the distal end of the catheter, the suction extension and/or catheter can be provided with a stop that limits the distal movement of the suction extension.

By replacing most of the length of the suction element with a control element, the device may have less friction when advanced relative to a suction catheter with a tube extending the whole length of the device since a control wire or other control element can offers less resistance for its movement. The tip of the suction extension can be given a curved tip to facilitate tracking of the device over a guidewire. Suction catheters with a curved tip have been found to improve tracking for a rapid exchange style catheter, as described in U.S. Pat. No. 8,021,351 to Boldenow et al., entitled "Tracking Aspiration Catheter," incorporated herein by reference. Thus, a suction extension for aspiration with a curved tip for tracking the tip over a guidewire can be effectively guided to difficult to reach locations with the use of a control wire or other control element moving the slide portion at or near the distal end of the suction extension, and the design provides for good suction ability without sacrificing the ability to reach difficult to reach vessels, such as within cerebral vessels. While the suction extension is moved, the guide catheter portion of the suction lumen can remain in place.

When suction is applied at or near the proximal end of the guide catheter with a suitable negative pressure device, fluid is sucked into a distal opening at the end of the suction extension. It has been found that surprisingly strong suction can be transmitted through to the suction extension. A suction lumen extends from a negative pressure device, generally attached at a fitting associated with a proximal section, at or near the proximal end of the suction system through the guide catheter lumen to the suction extension and through the proximal portion of the suction extension and the suction tip of the suction extension to the distal opening. Suitable negative pressure devices include, for example, syringes, pumps or the like. The guide catheter can provide a large lumen proximal section of the overall suction lumen. The effective suction lumen then can appear to have a large proximal section contributed by the guide catheter and a tapered distal section contributed by the suction extension, which can have one or more tapered segments.

The suction tip of the suction extension has a lumen with a reduced diameter relative to the guide catheter lumen and good flexibility to provide for placement of its distal end into smaller vessels. The lumen of the suction tip though is maintained at a sufficiently large diameter that provides for delivery of additional therapeutic devices through the lumen to the treatment location. Thus, the outer diameter of the suction tip generally is (diameter in mm=(Fr value)/3, Fr represents the French catheter scale) at least about 1.5 Fr less than the outer diameter of the distal section of the guide catheter. Based on bench testing and calculations presented below, the pressure drop from the proximal connection of the guide catheter with the negative pressure device and the distal tip of the suction extension can be surprisingly small. However, the decrease in diameter provides access to desirable vessels, such as cerebral vessels.

It was previously discovered that good suction properties could be obtained with a suction catheter with a stepped down diameter in a distal section. Thus, for example, the majority of the length of the suction catheter can be 6 Fr outer diameter while a distal section may be 5 Fr outer diameter, which roughly corresponding decreases in the inner diameters. Such a catheter can provide access into vessels suitable for a 5 Fr catheter, but can provide significantly better suction than a suction catheter with a 5 Fr catheter body along its entire length. Commercial stepped down suction catheters, such as Mi-Axus™ catheters (MIVI Neuroscience, Inc.) and ACE™ 64 catheters (Penumbra, Inc.) are finding good clinical results. The step down suction catheters and their use for thrombectomy procedures in cerebral arteries are described in published U.S. patent application 2012/0253313 A1 to Galdonik et al. (hereinafter the '313 application), entitled "Aspiration Catheters for Thrombus Removal," incorporated herein by reference. Comparisons of suction results from testing of these catheters are also presented below. While these catheters achieve better suction than catheters with constant diameters corresponding with the distal diameters, the present suction catheters with a sliding suction extension are found to provide surprisingly good suction suggesting that the diameter over the majority of the suction lumen length contributes to a large extent to the suction provided at the distal opening of the suction lumen. In particular, while the suction extension may have a longer length of the distal reduced diameter section, these features are more than compensated for by the longer length of the larger diameter guide catheter lumen that extends for a majority of the suction lumen.

Also described herein, a delivery catheter can provide a desirable very flexible distal tip with a narrow diameter that can track along a guidewire into particularly challenging positions in a vessel. For example, in regions of the cerebral vasculature, the arteries can twist and turn very significant amounts. To the extent that a guidewire can be placed at the target location, it still may be difficult to track a catheter or the like over the wire to the desired location. The delivery catheter described herein has an elastic distal section that can have an inner diameter comparable to the guidewire outer diameter so that it tracks closely over the wire which when combined with the desired flexibility provides for tracking. Once the delivery catheter is in place, desired additional medical devices can be tracked over the wire and through the delivery catheter for improved guidance of the device to the treatment location. To actually provide a delivered medical device for use at the treatment location, the medical device should be placed outside of the interior of the delivery catheter. The elasticity of the distal tip of the delivery catheter provides for the pushing of the delivered medical device past the elastic distal tip through the appropriate expansion of the elastic tip, which may or may not resume its narrow diameter following delivery of the medical device through the tip. Suitable medical devices for delivery include, for example, a suction tip associated with a suction system described herein, a microcatheter optionally associated with additional treatment structures, filters, angioplasty balloons, stent delivery devices, atherectomy devices or the like.

The proximal portion of the delivery catheter has a diameter selected to fit within a guide catheter, if relevant, and large enough to allow for delivery through its inner lumen of other percutaneous devices appropriate for delivery through to the treatment site. The elastic distal tip can have a suitable length to reach to appropriate treatment sights accounting for placement of its proximal end in an appropriate location based on its dimensions and flexibility. Since the distal tip may extend many times its original diameter to allow for delivery of medical devices through its lumen, the material forming the distal tip can be selected to stretch many times it diameter without tearing. It may or may not be desired for the elastic polymer to remain within its elastic limit such that it would resume its approximate original shape if the strain is withdrawn. For example, if the polymer is stretched beyond its elastic limit, the polymer remains distorted if the strain is removed. However, the polymers generally should be selected to be stretched to values below their elongation limit to prevent significant failure of the polymers and tearing to avoid any generation of debris within the vessel, although a sufficiently cohesive polymer may tear without creating a significant risk of fragmenting to leave debris in the vessel. Various biocompatible elastomers are suitable for the formation of the proximal portion of the delivery catheter as described further below.

An initial part of the procedure using the devices described herein generally involves accessing the treatment location within the vasculature. Guidewires have been designed to facilitate access to difficult to reach locations. The term guidewire is used herein to refer broadly to wire structures that may or may not have internal structure are referred to as guidewires whether or not they are formed from a solid or woven metal, such as corewire-overtube integrated structures, coils or the like which do not have a closed inner lumen over at least a portion of the devices length.

In particular, with the devices described herein procedures can be performed to provide re-profusion in vessels that are blocked completely or partially with clots. Clots in cerebral arteries can cause strokes with corresponding serious consequences, and time generally is of the essence of treating these conditions. The suction extension with the guide catheter can be used to provide aspiration that can be useful to remove clots or fragments thereof. Thus, the suction extension combined with the guide catheter and negative pressure device can be used as stand alone devices for thrombectomy procedures. However, the suction extension with aspiration can be effectively used as part of a treatment system comprising, for example, also a fiber based filter and/or other components to facilitate removal of a clot or portions thereof. The delivery catheter with the expandable tip is designed to facilitate access, so it is useful as a tool for the practice of various other procedures.

As demonstrated below, the aspiration system formed with a guide catheter and a suction extension provides enhanced suction ability within relatively narrow vessels downstream from the positioning of the guide catheter, such as cerebral vessels. The enhanced suction power can be valuable for the removal of clots from the vessel and thus can improve clinical results, whether used alone or used with additional components of a treatment system. As described below, the guide catheter based suction catheter can be used to generate good flow under aspiration through the tip of the suction extension and with a low pressure drop from the proximal connection of the negative pressure device to the distal opening of the catheter. With the combination of features, the catheter provides good access to smaller vessels, relative ease of placement and desirable degrees of suction power.

In some embodiments of the procedure, a guidewire can be placed at or near an occlusion and a guide catheter with a positionable suction extender can be placed in the vasculature upstream from the occlusion with the guidewire extending through the interior of the suction extender. If the suction catheter is to be used alone, then the suction extender can be advanced using a control wire over the guidewire to a suitable position near the clot. Then, with or without removing the guidewire, suction can be initiated to suck the clot or a portion thereof into the distal opening or against the tip of the suction extender. Suction may or may not be continued as the suction extender and/or guide catheter are removed from the patient.

While suction with the suction extension can be effective as the only device for clot removal, particularly effective systems can combine other devices for use with the suction catheter. In particular, a filter device can be used to provide both embolic protection as well as a tool to facilitate removal of the clot or portions thereof, which may involve direct engagement of the clot with the filter device. Fiber based filters/embolic protection systems have been developed that can be effectively used in the narrow vessels of interest. In particular, fiber-based filter systems with an appropriate actuation system can be used for delivery in a low profile configuration past an occlusion and deployed to provide protection from any clot fragments that may be released during the removal process.

The devices described herein provide improved functionality for performing procedures for the removal of clots from vessels. As noted herein, the devices can be used in various combinations within medical systems for percutaneous procedures.

Suction System With Extendable Suction Tip

Suction Systems are described that take advantage of good suction available with a suction catheter having a larger proximal suction lumen and a narrower diameter suction tip that uses the guide catheter lumen as a proximal suction lumen. A laterally slidable suction tip extends from a proximal section located within the guide lumen, and the suction tip can have a reduced diameter to provide access to narrow vessels while providing for delivery of other treatment structures and/or embolic protection structures as well as for a desirable level of suction for the removal of debris from the vessel. A control wire or other structure can be attached to the slidable suction tip to provide for selective lateral placement of the suction tip relative to a fixed guide catheter and a target treatment location. The catheter generally comprises structure, such as a seal, to limit flow through the guide catheter circumventing the suction tip and/or, such as a stop, to retain the proximal portion of the suction tip within the guide lumen at the distal end of the guide catheter. Some particular embodiments are shown in the figures as discussed in the following.

Referring to FIG. 1, suction system 100 comprises a suction adapted guide catheter 102 and a suction extension 104. The suction adapted guide catheter 102 comprises proximal section 106 and tubular shaft 108. Proximal section 106 generally is suitable for use also as a handle and generally can comprise a proximal fitting 120, a suction port 122 and an optional control wire port 124, as well as possibly other additional ports and/or fittings to provide desired functionality and access, in which all such ports and fittings can be arranged in a branch configuration or other suitable configuration. Proximal fitting 120 can comprise a suitable hemostatic valve, Luer fitting or the like to provide for entry of a guidewire and/or structures delivered over the guidewire into the guide catheter lumen, such as alternative treatment structures and/or embolic protection devices. Suitable embolic protection devices can be mounted on a guidewire. Suitable treatment structures are described further below and can include, for example, stents, stent retrievers, atherectomy devices or the like. As shown in FIG. 1, a negative pressure device 126 is shown connected with suction port 122, and suitable negative pressure devices include, for example, syringes, pumps, such as peristaltic pumps, piston pumps or other suitable pumps, aspirator/venturi, or the like.

Tubular shaft 108 can have an approximately constant diameter along its length, or the guide catheter can have sections with different diameters, generally with a smaller diameter section distal to a larger diameter section. Tubular shaft 108 can have one or more radiopaque marker bands to facilitate positioning of the tubular shaft within the patient, and FIG. 1 shows a marker band 128 near the distal end of tubular shaft 108, although alternative positions can be used as desired. At or near the distal end of the shaft, a stop 130 is positioned to retain a portion of suction extension 104 within the lumen of tubular shaft 108. Suitable designs of stop 130 are presented below. Tubular shaft 108 can further comprise a seal 132 to provide for reducing or eliminating any flow within tubular shaft 108 that avoids suction extension 104. In some embodiments, seal 132 can be combined with stop 130, or seal 132 as a distinct element can be avoided through a design with a sufficiently tight fit between suction extension 104 and the lumen wall of tubular shaft 108. As described below, tubular shaft 108 can have coatings on the inner surface and/or the outer surface or portions thereof.

Suction extension 104 comprises a proximal portion 140, suction tip 142, connection portion 144, optional engagement element 146 and control structure 148, such as a control wire. All or a part of proximal portion 140 can be configured to remain within the lumen of guide catheter 102. As shown in FIG. 1, proximal portion 140 comprises a radiopaque marker band 152, although proximal portion may not have a marker band in some embodiments and in other embodiments can comprise a plurality of marker bands, and suction tip 142 is shown with radiopaque marker band 154 near the distal tip of suction tip 142, although again suction tip 142 can comprise a plurality of radiopaque marker bands if desired. Connection portion 144 connects proximal portion 140 and suction tip 142, which can be a transition portion that gradually changes diameter or a connector that forms a seal between the proximal portion and suction tip. Optional engagement element 146 can engage stop 130 to establish the distal placement limit of suction extension 104 relative to guide catheter 102. In some embodiments, stop 130 is configured to engage an edge or other limiting structure of proximal portion 140 so that engagement element 146 is effectively integrated with the proximal portion 140 or connection portion 144. Control structure 148 can be a control wire or the like that connects with proximal portion 140 and extends exterior to the catheter, such as exiting through control wire port 124. Control structure 148 can be used to control positioning of proximal portion 140 within the lumen of tubular shaft 108. Control structure 148 can comprise a control tool 156, such as a handle, slide or other the like that can anchor a control wire or other connecting element to facilitate movement of the control wire. In some embodiments, alternative structures such as a plurality of wires or wire cylindrical assembly can connect the proximal portion to the proximal end of the suction catheter system to provide a desired level of control with respect to positioning the proximal section.

Figure 2:
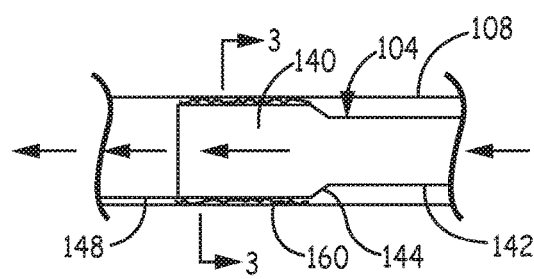
FIG. 2 is a fragmentary side view of an expanded portion of the catheter system of FIG. 1 showing the interface of the suction extension with the guide catheter.
Figure 3:
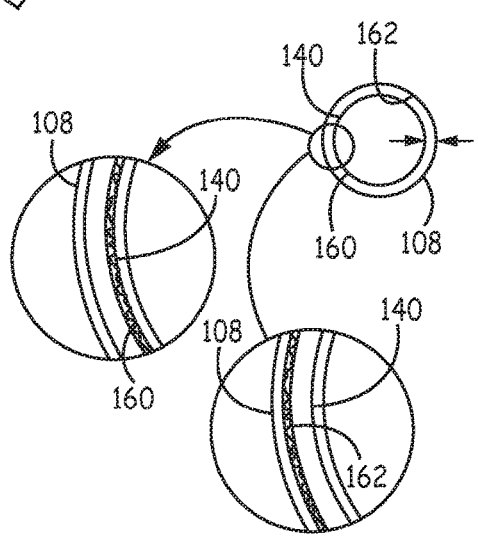
FIG. 3 is a sectional view taken along line 3-3 of FIG. 2 with two inserts showing expanded views of two embodiments with coatings.

Referring to FIG. 2, an expanded view is presented of the interface between tubular shaft 108 and proximal portion 140 of suction extension 104. A cross sectional view is shown in FIG. 3. Several seals are described in the subsequent figures to reduce or eliminate flow between the inner surface of tubular shaft 108 and the outer surface of proximal portion 140. Flow arrows indicate desired flow directions when suction is applied. However, in some embodiments, the clearance can be made sufficiently small between the outer surface of proximal portion 140 and the inner surface of tubular shaft 108. For example, the tolerance measured as a difference between the adjacent inner surface and outer surface can be, for example, no more than about 5 mils (1 mil=1/1000 of an inch; 5 mil~127 microns), and in further embodiments, no more than about 4 mils (101.6 microns) or in additional embodiments no more than about 3 mils (76.2 microns), and can be approximately zero within the measurement uncertainty. A person of ordinary skill in the art will recognize that additional ranges within the explicit ranges of tolerances above are contemplated and are within the present disclosure. A lubricious coating 160 (see left insert of FIG. 3), which may or may not be a hydrophilic coating, can be placed on the outer surface of the proximal portion 140, and/or a lubricious coating 162 (see right insert of FIG. 3) can be placed on the inner surface of tubular shaft 108 to facilitate longitudinal movement of the suction extension 104 with a low tolerance friction fit. Suitable coatings include, for example, hydrophobic coatings such as polytetrafluoroethyelene, or other fluoropolymers, or hydrophilic coatings, such as polyvinyl alcohol. Suitable coatings can include, for example, a gel or fluid, such as polyfluoropolyether fluid or triglycerides that can be applied at the time of use.

Figure 4:
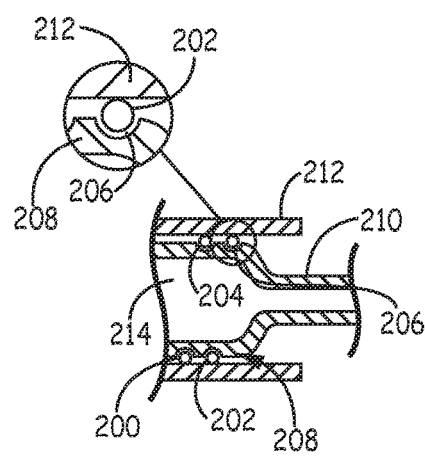
FIG. 4 is a fragmentary side view of an embodiment of a seal between the suction expansion and the guide catheter comprising o-rings.

It can be desirable to include specific structural elements to effectuate the seal rather than relying only on friction/coatings. Various embodiments of seal 132 are shown in FIGS. 4-15. Referring to FIG. 4, a portion of a catheter is shown indicating the use of o-rings to form the seal. Specifically, o-rings 200, 202 are positioned within grooves 204, 206 along the surface of proximal portion 208 or suction extension 210. O-rings 200, 202 engage inner surface of tubular shaft 212 to form the seal such that flow is confined to suction lumen 214. While FIG. 4 shows two adjacent o-rings, a seal can comprise a single o-ring, such as either 200 or 202 alone, or three or more o-rings. O-rings can be formed from suitable materials, such as biocompatible elastic polymers, examples of which are provided in the materials summary below.

Figure 5:
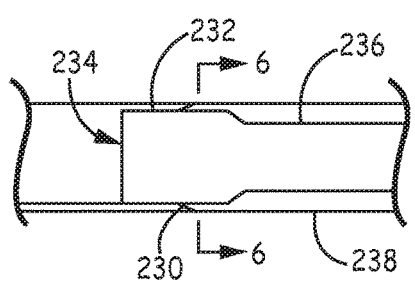
FIG. 5 is a fragmentary side view of an embodiment of a seal between the suction expansion and the guide catheter comprising an elastic seal.
Figure 6:
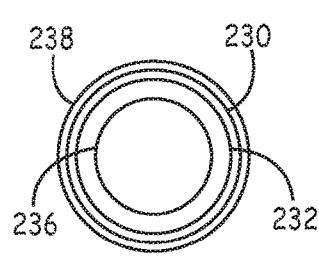
FIG. 6 is a sectional view taken along line 6-6 of FIG. 5.

Referring to FIGS. 5 and 6, an elastic seal 230 is provided around proximal portion 232 of suction extension 234 in which suction tip 236 extends in a distal direction. Elastic seal 230 can be secured to proximal portion 232 with adhesive, heat bonding, or other suitable technique. Elastic seal 230 can provide for relative movement of suction extension 234 and shaft 238 due to the elasticity. Elastic seal 230 can be angled, arched or other suitable configuration. Elastic seal 230 can be formed form elastic polymers presented below.

FIGS. 7A-11 display embodiments in which sealing is based on minor distortion of the catheter elements to releasably engage the shaft with the proximal element of the suction extender to block potential flow between the elements. The different figures involve distinct mechanism to provide corresponding forces to engage the elements. For these embodiments, the sealing engagement is generally performed once the suction extension is laterally placed at a desired position.

Figure 7A:
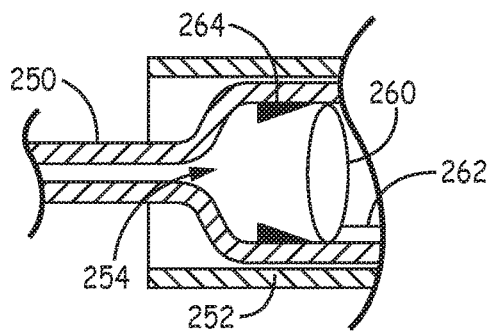
FIG. 7A is a fragmentary side view of an interface between a suction extension and guide catheter comprising a seal involving elastic deformation based on movement of a slidable loop, shown in the unsealed configuration.
Figure 7B:
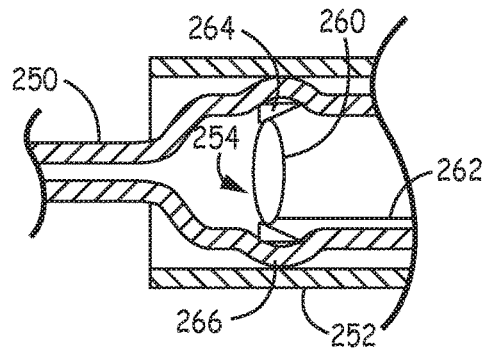
FIG. 7B is a fragmentary side view of the sealing structure of FIG. 7A shown in the sealed configuration.

Referring to FIGS. 7A and 7B, suction extension 250 engages guide catheter 252 with an engageable sealing element 254. Sealing element 254 comprises a slidable loop 260 controllable with a loop control wire 262 that engages a circular ramp 264. Loop control wire 262 extends in a proximal direction and edits the catheter through a proximal port so that the medical professional using the catheter can control the engagement of the seal through positioning of the loop. When slidable loop 260 in a proximal position, as shown in FIG. 7A, the seal is unengaged and suction extension 250 can more longitudinally within the lumen of guide catheter 252. Referring to FIG. 7B, when slidable loop is positioned in a distal direction, slidable loop 260 engages circular ramp 264 and forms a bulge 266 that engages the inner wall of guide catheter 252 to form a seal. Bulge 266 does not need to physically extend very far since the clearance between suction extension 250 and guide catheter 252 can be small.

Figure 8A:
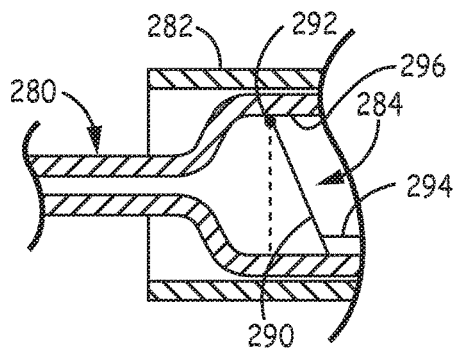
FIG. 8A is a fragmentary side view of an interface between a suction extension and a guide catheter with an elastic deformation based seal incorporating a pivot ring to selectively activate the seal, shown in an unsealed configuration.
Figure 8B:
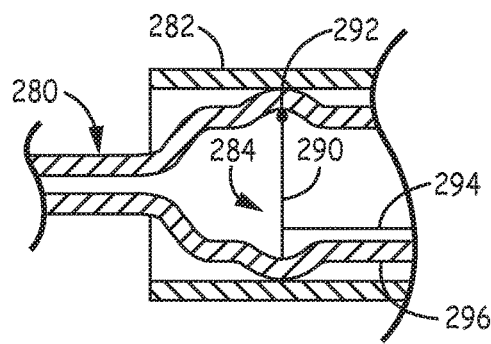
FIG. 8B is a fragmentary side view of the sealing structure of FIG. 8A shown in the sealed configuration.

A similar structure is shown in FIGS. 8A and 8B based on a pivoting loop. In this embodiment, suction extension 280 engages guide catheter 282 with deforming sealing element 284. Deforming sealing element 284 comprises ring 290, secured at pivot 292 and control wire 294. Ring 290 has an outer diameter somewhat larger than inner diameter of proximal portion 296 of suction extension 280 and an inner diameter in some embodiments can be at least as large as the inner diameter of proximal portion 296. Control wire 294 can be used to pivot ring 290 to an engaged configuration shown in FIG. 8B where suction extension 280 deforms slightly at the position of the ring to form a seal with guide catheter 282. Control wire 294 extends in a proximal direction to exit the catheter at a proximal fitting. In alternative embodiments, the unengaged position of ring 290 can be in a distal orientation relative to pivot 292 so that the control wire can be pulled to engage the seal.

Figure 9A:
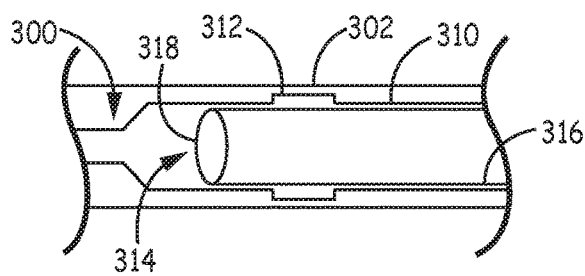
FIG. 9A is a fragmentary side view of an interface between a suction extension and a guide catheter with an elastic deformation based seal incorporating a deformable element of the suction extension activated with a pullable actuation element, shown in an unsealed configuration.
Figure 9B:
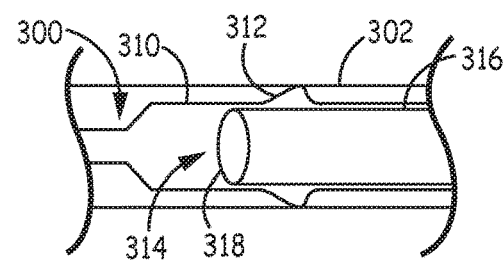
FIG. 9B is a fragmentary side view of the sealing structure of FIG. 9A shown in the sealed configuration.

Referring to FIGS. 9A and 9B, a seal is shown based on a deformable section of the proximal portion of the aspiration extension. FIG. 9A depicts the relevant portion of the device in the un-deformed configuration, and FIG. 9B depicts the relevant portion of the device in the deformed and sealed configuration. Suction extension 300 is positioned within guide catheter 302. Suction extension 300 comprises proximal section 310 having a deformable element 312, and an actuation element 314. Deformable element 312 can have a bridge shaped cross section and can be formed from a distinct material and/or have a distinct structure providing for deformation upon application of suitable forces. The bridge shaped cross section can be rectangular, square, elliptical, round, or more complex shapes, such as an "M" shape, and can be of a suitable catheter material, which can be the same or different relative to the remaining portion of the catheter. As shown in FIGS. 9A and 9B, actuation element 314 comprises inner sleeve 316 secured to proximal section 310 at anchor point 318. Inner sleeve 316 extends proximally to the exterior of the catheter through a fitting such that relative movement of inner sleeve 316 and a control wire (not shown for this embodiment) controlling the position of proximal section 310 applies force that can deform deformable element 312. Inner sleeve is used to transmit force and may be generally cylindrical or other shape that provides for appropriate force transfer. Deformable element 312 may or may not provide for substantial restoration of the deformable element to its original configuration upon the reversal of forces used to deform the deformable element.

Figure 10A:
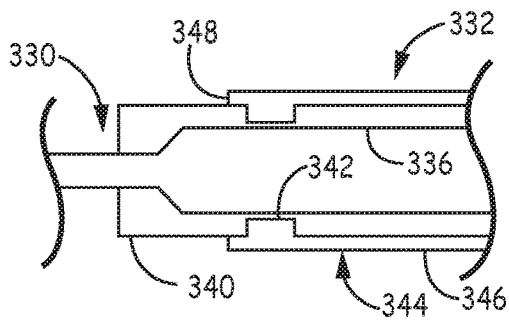
FIG. 10A is a fragmentary side view of an interface between a suction extension and a guide catheter with an elastic deformation based seal incorporating a deformable element of the guide catheter activated with a pullable actuation element, shown in an unsealed configuration.
Figure 10B:
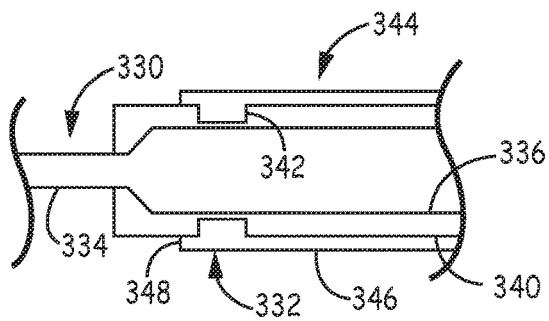
FIG. 10B is a fragmentary side view of the sealing structure of FIG. 10A shown in the sealed configuration.

Referring to FIGS. 10A and 10B, a complementary embodiment is shown in this a deformable element is formed as a portion of the guide catheter rather than the suction extension. Suction extension 330 extends within guide catheter 332. Suction extension comprises suction tip 334 and proximal section 336. Guide catheter 332 comprises catheter body 340, deformable element 342 and actuation element 344. As shown in FIGS. 10A and 10B, actuation element 344 comprises an outer sleeve 346 secured to catheter body 340 at anchor point 348. As with deformable element 312 of FIGS. 9A and 9B, deformable element 342 may or may not provide for substantial restoration of the deformable element to its original configuration upon the reversal of forces used to deform the deformable element. As with inner sleeve 316, outer sleeve 346 is used to transmit force and may be generally cylindrical or other shape that provides for appropriate force transfer.

Figure 11:
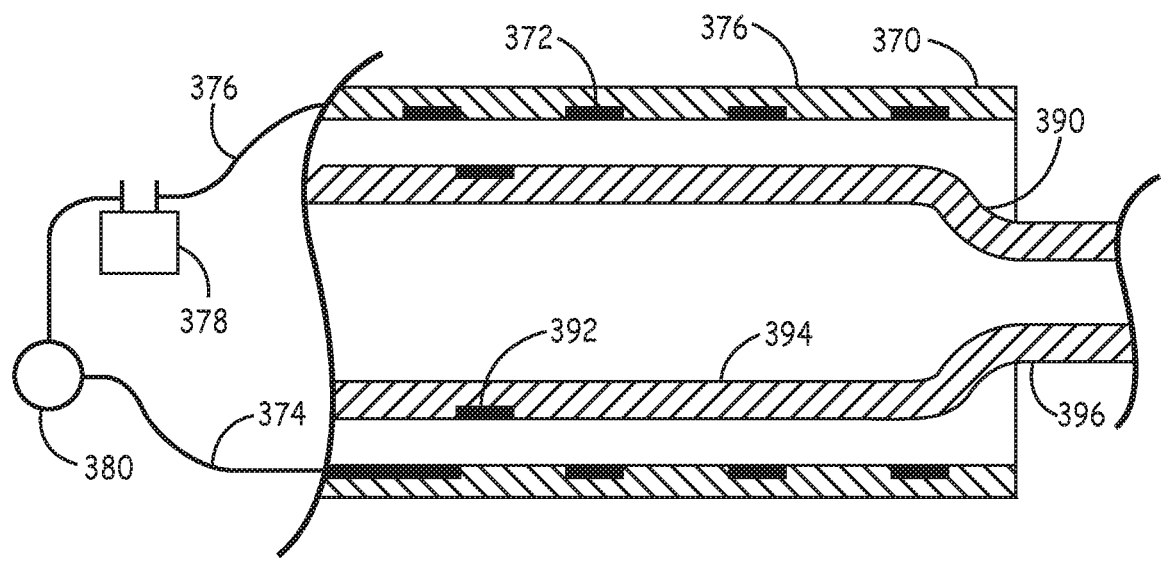
FIG. 11 is a fragmentary side view of an interface between a suction extension and a guide catheter with an elastic deformation based seal with an electromagnetic actuatable seal.

FIG. 11 shows a catheter and suction extension with a magnetic based seal. Guide catheter 370 comprises a metal coil 372 embedded in the polymer wall of the catheter. Metal coil is connected to electrical wires 374, 376 that are electrically insulated from each other and extends down the length of the catheter to a proximal section (not shown). Electrical wires 374, 376 are connected to metal coil 372 such that current can flow between electrical wires 374, 376 along all or a majority of the metal coil such that the current generates an electrical field. At the proximal end of electrical wires 374, 376, electrical wires 374, 376 are connected to a power source 378, such as a battery, through a switch 380. Suction extension 390 comprises a permanent magnet 392 embedded in a polymer wall of proximal section 394 and suction tip 396 extends in a distal direction from proximal section 394. When switch 380 is turned to the on position by a medical professional, current flows through metal coil 372 to generate a magnetic field that attracts permanent magnet 392 to distort the wall of proximal section 394 and form the seal. Turning switch 380 to off can relax the seal such that suction extension 390 can move longitudinally within guide catheter 370.

Figure 12:
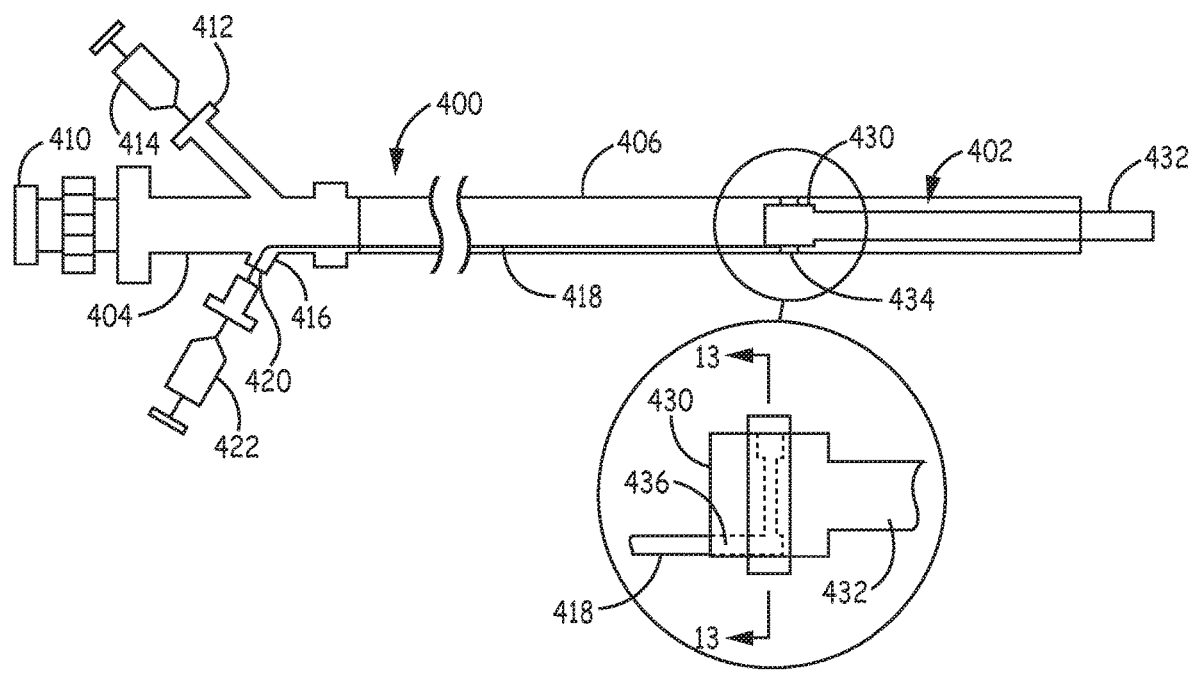
FIG. 12 is a side view of a suction system comprising an interface between a suction extension and a guide catheter with a balloon based seal.

A balloon based seal is shown in the embodiment of FIG. 12. The suction system comprises guide catheter 400 and suction extension 402. Guide catheter 400 comprises proximal section 404 and tubular shaft 406 connected at or near the distal end of proximal section 404. Proximal section 404 comprises a proximal fitting 410, a branched connector 412 for connection to a suction device 414 and a branched connector 416 for passage of tube 418 through a diaphragm seal or the like 420 in which tube 418 is connected to a fluid source 422 for inflating and deflating a balloon seal. Diaphragm seal 420 or a suitable hemostatic fitting can be made of rubber or other suitable material or construction so that tube 418 can be moved in and out from the interior of guide catheter 400 with little or no blood loss. Suction extension 402 comprises a proximal section 430 and suction tip 432.

Figure 13:
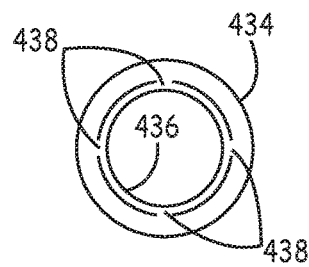
FIG. 13 is a section view of the balloon based seal taken along line 13-13 of FIG. 12.

Referring to the expanded insert of FIG. 12, balloon 434 is located around the circumference of proximal section 430. Tube 418 can connect directly to balloon 434 or as shown in FIGS. 12 and 13 to a channel 436 that extends within proximal section 430 in which the channel is in fluid connection to the interior of balloon 434 through one or more openings 438. Thus, when fluid is injected from fluid source 422, balloon 434 inflates and subsequent removal of fluid back into fluid source 422 or an alternative fluid reservoir, then balloon 434 deflates. Inflation of balloon 434 forms a controllable seal at the contact point of balloon 434 and tubular shaft 406.

Figure 14:
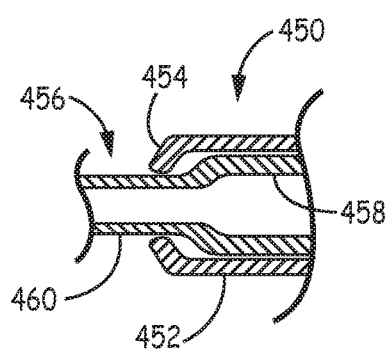
FIG. 14 is a fragmentary side view of a structure providing simultaneous stop and seal functions.
Figure 15:
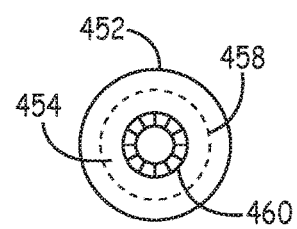
FIG. 15 is an end view from the distal end of the suction system of FIG. 14 with dashed lines showing the outer diameter of the proximal portion of the suction extension.

As noted above, the guide catheter generally comprises a stop that retains at least a significant portion of the proximal section of suction extension within the lumen of the shaft of the guide catheter. In some embodiments, the seal and the stop elements are combined in a single structure, such as shown in FIGS. 14 and 15. Referring to FIG. 14, guide catheter 450 comprises tubular shaft 452 with, at its distal end, an elastic seal 454 having sufficient mechanical rigidity to also function as a stop. Suction extension 456 has a proximal portion 458 and suction tip 460 extending outward from guide catheter 450 through elastic seal 454. For example, as shown in FIG. 14, elastic seal 454 can have elastic polymer contacting suction tip 460 and optionally a more rigid material, such as thermoplastic polymer, metal or other appropriate material, connecting to tubular shaft 452.

Figure 16:
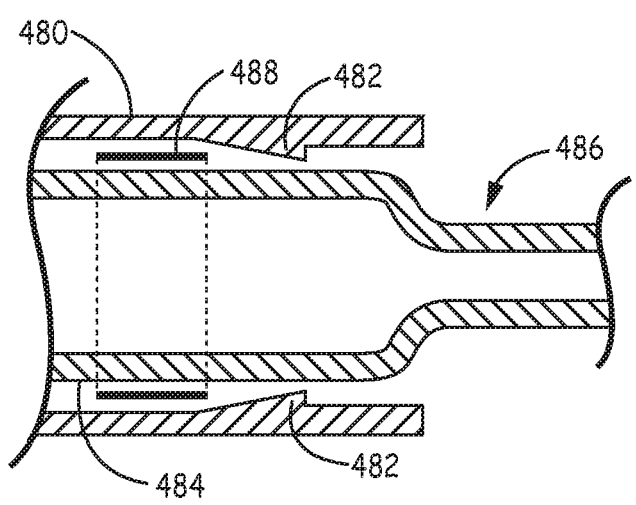
FIG. 16 is a fragmentary side view of a stop design for the engagement of a ridge along the inner diameter of a guide catheter with a widening section along the outer surface of a proximal portion of s suction extension.

Another embodiment of a stop is shown in FIG. 16. In this embodiment, tubular shaft 480 of the guide catheter comprises a ridge 482 that narrows the inner diameter of tubular shaft 480 at a location at or near the distal end of tubular shaft 480. Ridge 482 may or may not go around the circumference of the inner wall of tubular shaft 480, and in some embodiments may be only at 1, 2, 3, 4 or other number of specific locations around the circumference. As shown in FIG. 16, the narrowed inner diameter at ridge 482 (evaluated at diameter through the center of the shaft connecting isolated points providing the narrowing in appropriate embodiments) is wider than the outer diameter of proximal section 484 of suction extension 486. Widening structure 488 along the exterior of proximal section 484 provides a diameter that exceeds the narrowed inner diameter at ridge 482 so that widening structure 488 cannot pass ridge 482 so that ridge 482 functions as a stop. Widening structure 488 can be, but may not be, portions of a balloon seal or other seal components, or widening structure 488 can be provided just to provide the stop function. Widening structure 488 may or may not go around the entire circumference of proximal section 484, but widening structure 488 and ridge 482 can be designed to provide sufficient circumferential coverage so that they cannot circumvent the stop function of the elements.

A similar stop design is shown in FIGS. 17 and 18. In this embodiment, tubular shaft 500 has a lip 502 at the distal opening, although in alternative embodiments, the lip can be moved inside the inner lumen of tubular shaft 500 reasonably near the distal opening. Lip 502 reduces the diameter at the lip to a value less than the outer diameter of proximal section 504 of suction extension 506 with suction tip 508 extending in a distal direction. Due to the reduced diameter at lip 502, it functions as a stop.

Referring to FIGS. 19-21, the stop function is provided by a track that interfaces tubular shaft 520 and suction extension 522. FIG. 19 is a sectional exploded view that cuts the elements through the central axis to render the track elements visible. Referring to tubular shaft 520 in FIGS. 19 and 20, the inner surface of the wall is contoured to have two channels 524, 526 that end prior to the distal end of tubular shaft 520. Referring to FIGS. 19 and 21, suction extension 522 comprises proximal section 530 and suction tip 532, and proximal section 530 has two ridges 534, 536. Ridges 534, 536 fit within channels 524, 526 so that channels limit the movement of ridges 534, 536 and correspondingly the relative movement of suction extension 522 so that the distal termination of channels 524, 526 function as a stop.

Referring to FIG. 1, in some embodiments a control structure, such as a control wire, interfaces with the proximal portion of the suction extension. Referring to FIG. 22, an embodiment is shown in which suction extension 550 has a control wire 552 with its distal end embedded within the polymer wall of proximal portion 554. Suction tip 556 extends in a distal orientation relative to proximal portion 554. As described further below, the polymer walls of components of a suction extension can comprise braided and/or coiled wires embedded within the polymer walls. Referring to the expanded view in the balloon insert, the embedded end of control wire 552 is shown under the embedded braiding/coil reinforcement 558, which can further secure control wire 552 to proximal portion 554. In alternative embodiments such as shown in FIG. 12, a tube or other structure can be used in addition to or as an alternative to a control wire, and such a tube can be securely attached to a proximal portion with suitable reinforcements and can also be under a portion of braiding or coil if desired.

Figure 23:
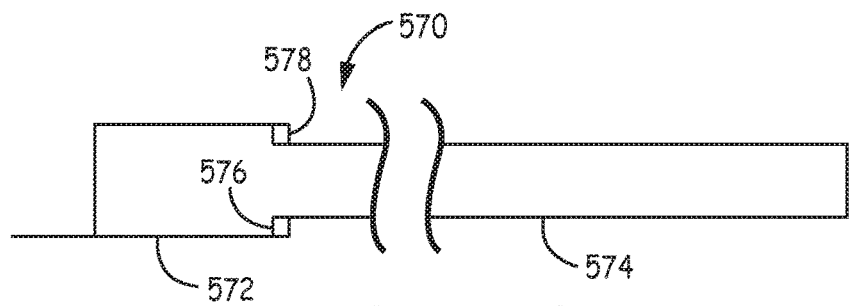
FIG. 23 is a side view of a suction extension embodiment having low or no extent transition portion with reinforcement.
Figure 24:
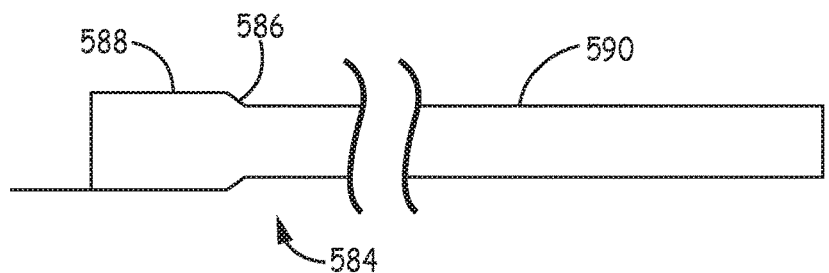
FIG. 24 is a side view of a suction extension embodiment with a gradual tapered transition portion.

As noted above, the suction extension has a connection portion connecting the proximal portion and the suction tip, and the design may generally depend on manufacturing selections. Referring to FIG. 23, an embodiment of suction extension 570 has a connection portion essentially no transition region connecting proximal portion 572 and suction tip 574. Basically, wall 576 connects suction tip 574 to proximal portion 572. An optional reinforcement 578, such as a polymer or metal element at the connection, can be used to help secure the elements. Referring to FIG. 24, an embodiment of suction extension 584 has a transition portion 586 connecting proximal portion 588 with suction tip 590. As shown in FIG. 24, transition portion provides an approximately linear transition of diameters from the wider diameter of proximal portion to the narrower diameter of suction tip 590. In alternative embodiments, a transition portion can have nonlinear changes in diameter if desired, but the change is generally monotonic. The transition regions can be formed through an extrusion process or through confirming of a thermoplastic polymer to a mandrel shape or other suitable process approach known in the art.

A significant aspect of the suction extension is the narrower diameter suction tip. The effective suction lumen then extends through the guide catheter into the proximal portion of the suction extension and then into the suction tip. The narrow diameter of the suction tip provides for reach into small circuitous blood vessels and the use of the larger diameter proximal suction lumen improves the suction performance significantly without detracting from the ability to reach appropriate locations. To further provide for suction strength, the suction tip itself can have different sections with stepped down diameters. In general, the arteries progressively decrease in diameter so a section with a somewhat larger diameter may be desirable consistent with the reach of the suction tip into a selected narrow vessel.

Figure 25:
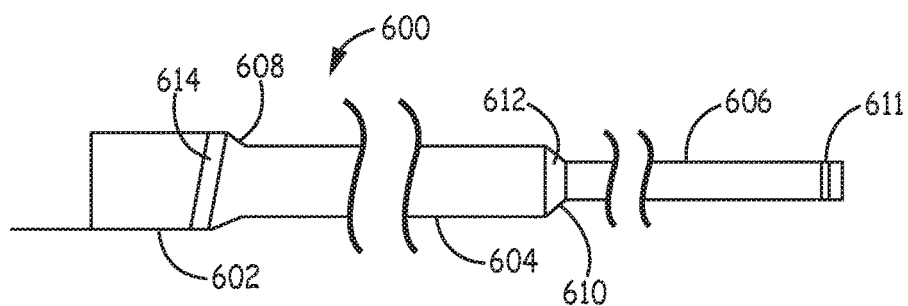
FIG. 25 is a side view of a suction extension embodiment having a suction tip with two successively narrowed sections.

Referring to an embodiment shown in FIG. 25, suction extension 600 comprises proximal portion 602, first tip section 604, distal tip section 606, first optional transition section 608 and second optional transition section 610. Proximal portion 602 can be any of the various embodiments described above with corresponding seal structures. Similarly, optional transition section 608 and 610 can have transition structures as described above or independently replaced with a connection structure such as shown in FIG. 23. Dimensions overall of the proximal portion and suction tip are described further below. With respect to first tip section, this section generally has an approximately constant diameter that is generally from about $[d+0.9(D-d)]$ to about

[d+0.1(D−d)], in further embodiments from about [d+0.75(D−d)] to about [d+0.25(D−d)], and in some embodiments from about [d+0.65(D−d)] to about [d+0.35(D−d)], where d is the diameter of distal tip section 606 and D is the average diameter of proximal portion 602. The length of first tip section can be from about 10% to about 90%, in further embodiments from about 20% to about 80% and in additional embodiments form about 30% to about 70% of the total length of suction tip, i.e., the total length of first tip section 604, distal tip section 606, first optional transition section 608 and second optional transition section 610. A person of ordinary skill in the art will recognize that additional ranges of relative dimensions within the explicit ranges above are contemplated and are within the present disclosure. This embodiment is shown with 3 radiopaque marker bands, marker band 611 near the distal tip, marker band 612 near the second (distal) transition position and marker band 614 near the first (proximal) transition region. While FIG. 25 shows one intermediate tip section between proximal portion and the distal tip section, in other embodiments there can be multiple constant diameter intermediate sections which divide the length available for the intermediate sections specified above and on average have the diameters for the intermediate section specified above, for example, there can be two intermediate sections, three intermediate sections or more than three intermediate sections.

Figure 26:
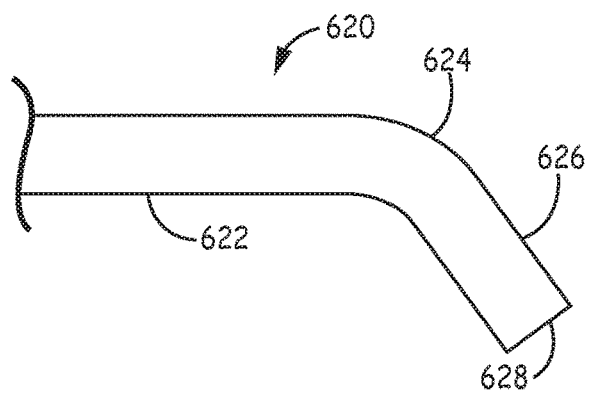
FIG. 26 is a fragmentary side view of a suction tip with a bend.
Figure 27:
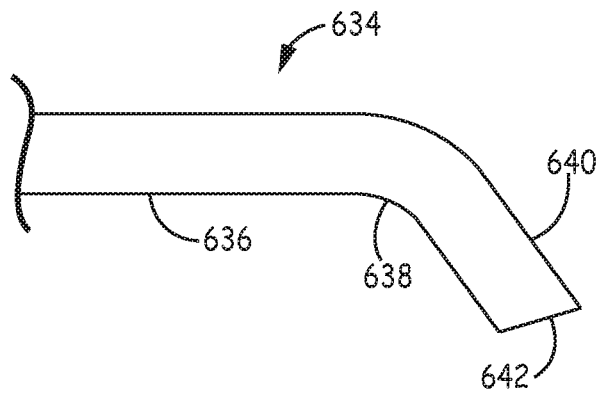
FIG. 27 is a fragmentary side view of a suction tip with a bend and an angled opening.

Regardless of whether or not the suction tip includes intermediate sections, the distal tip of the catheter can be bent or curved in its natural unstressed configuration. It has been found that a bent tip catheter can facilitate tracking of the catheter over a guidewire without adversely altering the suction abilities. See U.S. Pat. No. 8,021,351 to Boldenow et al., entitled "Tracking Aspiration Catheter," incorporated herein by reference. Two version of a bent tip suction tip are shown in FIGS. 26 and 27. Referring to FIG. 26, suction tip 620 comprises a straight section 622, bend 624 and bent tip section 626 with a flat distal opening 628 approximately perpendicular to the axis of bent tip section 626. Referring to FIG. 27, suction tip 634 comprises a straight section 636, bend 638 and bent tip section 640 with an angled distal opening 642 at a non-perpendicular angle to the axis of bent tip section 640. Bent tip sections 626, 640 are generally cylindrical and can have approximately the same diameters as corresponding straight sections 622, 636. While two shapes of openings are shown in FIGS. 26 and 27, any reasonable shape of the opening generally can be used.

The angle of the curved tip relative to a straight tip generally is less than 90 degrees and can be, for example, from about 10 degrees to about 60 degrees and in further embodiments from about 25 degrees to about 50 degrees. The selected angle corresponds with a radius of curvature, and the radius of curvature can be, for example, from about 3 mm to 20 mm and in further embodiments from about 4 mm to about 16 mm. In some embodiments, a straight portion of the tip after the curve can have a length no more than about 1 cm, and in other embodiments from about 0.1 mm to about 6 mm and in further embodiments from about 0.5 mm to about 4 mm. In alternative embodiments, the curve consists of a gradual arc with no significant straight section distal to it, such that the curve or bend is specified by the angle and radius of curvature. A person of ordinary skill in the art will recognize that additional ranges of angles, radii and lengths within the explicit ranges above are contemplated and are within the present disclosure.

Proximal portion of suction extension provides a transition of the suction lumen from the guide catheter to the suction tip. As noted above, the proximal portion generally is associated with a seal and may be designed to be constrained within the lumen of the guide catheter with a stop. The lateral extent of the proximal portion should be sufficient to provide mechanical stability within the guide catheter lumen, but otherwise does not need to be particularly long. In general, the proximal portion can have a lateral extent from about 5 millimeters (mm) to about 25 centimeters (cm), in further embodiments from about 8 mm to about 20 cm and in other embodiments from about 1 cm to about 18 cm. The outer diameter of the proximal section can be close to the inner diameter of the guide catheter, and with respect to the average inner diameter of the proximal section, it can be from about 80% to about 97% of the inner diameter of the guide catheter, in further embodiments from about 82% to about 95% and in additional embodiments from about 84% to about 93% of the inner diameter of the guide catheter. The diameter of the proximal portion may or may not be approximately constant, and structure, such as a small gradual taper or sections with step down diameters generally may be acceptable. The division of the proximal portion and a transition zone may be somewhat arbitrary, although the proximal portion is generally associated with the seal. A person of ordinary skill in the art will recognize that additional ranges of proximal portion dimensions within the explicit ranges above are contemplated and are within the present disclosure.

The suction tip or distal suction tip for appropriate embodiments can have an inner diameter from about 20 percent to about 90 percent of the inner diameter of the tubular shaft of the guide catheter, and in further embodiments from about 30 percent to about 85 percent and in additional embodiments from about 35 percent to about 80 percent of the average diameter of the tube. For example, the distal tip can have an inner outer diameter range from about 0.667 mm to about 2 mm, in further embodiments from about 0.85 mm to about 1.9 mm, and in other embodiments from about 0.9 mm to about 1.75 mm. The distal tip can have a length from about 3 cm to about 50 cm, in some embodiments from about 5 cm to about 40 cm and in further embodiments from about 8 cm to about 35 cm. The guide catheter can have an outer diameter from about 5.5 Fr (1.667 mm diameter) to about 10 Fr (3.333 mm diameter), in further embodiments from about 6 Fr (1.833 mm diameter) to about 9 Fr (3 mm diameter), and in some embodiments from about 6.25 Fr (2 mm diameter) to about 8.5 Fr (2.833 mm diameter). The guide catheter measurement are generally referenced to the outer diameter, and the inner diameter is less than the outer diameter by twice the wall thickness. The length of the guide catheter can be from about 30 cm to about 150 cm, in further embodiments from about 35 cm to about 130 cm and in additional embodiments from about 40 cm to about 120 cm. The length of tubular shaft can be from about 30 cm to about 150 cm, in further embodiments from about 35 cm to about 130 cm and in additional embodiments from about 40 cm to about 120 cm. A person of ordinary skill in the art will recognize that additional ranges of dimensions within the explicit ranges above are contemplated and are within the present disclosure.

Catheter components can be formed from one or more biocompatible materials, including, for example, metals, such as stainless steel or alloys, e.g., Nitinol®, or polymers such as polyether-amide block co-polymer (PEBAX®), nylon (polyamides), polyolefins, polytetrafluoroethylene, polyesters, polyurethanes, polycarbonates, polysiloxanes (silicones), polycarbonate urethanes (e.g., ChronoFlex AR®), mixtures thereof, or other suitable biocompatible polymers. Radio-opacity can be achieved with the addition of metal markers, such as platinum-iridium alloy, tantalum, tungsten, gold, platinum-tungsten alloy or mixtures thereof, such as wire or bands, or through radio-pacifiers, such as barium sulfate, bismuth trioxide, bismuth subcarbonate, powdered tungsten, powdered tantalum or the like, added to the polymer resin. Generally, different sections of aspiration catheter can be formed from different materials from other sections, and sections of aspiration catheter can comprise a plurality of materials at different locations and/or at a particular location. In particular, it may be desirable to form seal components from an elastomeric polymer, such as suitable polyurethanes, polydimethyl siloxane and polytetrafluoroethylene. In addition, selected sections of the catheter can be formed with materials to introduce desired stiffness/flexibility for the particular section of the catheter. Similarly, fitting can be formed from a suitable material, such as one or more metals and/or one or more polymers.

Figure 28:
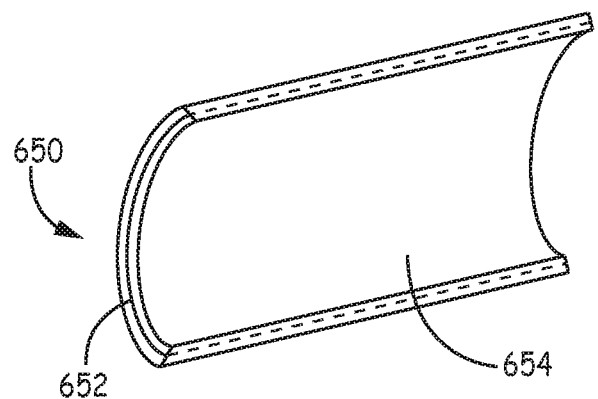
FIG. 28 is a cut-away portion of a catheter wall showing some features of its construction.

In some embodiments, the guide catheter, suction extension or appropriate portions thereof comprises a thermoplastic polymer with embedded metal elements, which reinforces the polymer. Suitable polymers include, for example, polyamides, i.e., nylons, polyolefins, or the like. The wire can be braided, coiled or otherwise placed over a polymer tubing liner with some tension to keep the wire in place over the tubing liner. A cutoff portion of a reinforced catheter section is shown in FIG. 28, in which catheter section 650 has metal reinforcement 652 embedded in the polymer wall 654. In some embodiments, suction tip can comprise both braided wire and a metal coil, which provide desirable flexibility and resilience to the element as well as mechanical strength with a thin wall. A polymer jacket, such as a heat shrink polymer, can then be placed over the top or the polymer softened to allow incorporation of the metal reinforcements. Upon heating to a temperature over the softening temperature or heat shrink temperature of the polymer and subsequent cooling, the wire becomes embedded within the polymer. In appropriate embodiments, the liner and jacket can be the same or different materials. Suitable wire includes, for example, flat stainless steel wire or the like. Wire diameters can range from about 0.00025 inch (0.00635 mm) to about 0.004 inch (0.1 mm) and in further embodiments from about 0.0005 inch (0.013 mm) to about 0.003 inch (0.075 mm). Braid picks per inch can be from about 20 to about 250 picks per inch and in further embodiments from about 50 to about 150 picks per inch. Coils can be single or multiple filament coils having, for example, pitches from about 0.005 inch (0.13 mm) to about 0.1 inch (2.54 mm) and in further embodiments from about 0.01 inch (0.26 mm) to about 0.050 inch (1.27 mm). A person of ordinary skill in the art will recognize that additional ranges within the explicit ranges below are conceived and are within the present disclosure. The wire adds additional mechanical strength while maintaining appropriate amounts of flexibility. The wire can provide some radio-opacity although radiopaque bands generally would provide a darker and distinguishable image relative to the wire. However, the image of the wire can provide further visualization of the catheter during the procedure.

To decrease the chance of accidental removal of the radiopaque band from the catheter and to decrease the chance of the radiopaque band catching onto other objects within the vessel, a metal reinforcing wire can be used to cover or enclose the radiopaque band with the metal wire subsequently being embedded within the polymer. As described in the previous paragraph, the metal wire can comprise interwoven wires, coil, combinations thereof, or the like. A polymer jacket can be placed over the metal wire, which is correspondingly covering the radiopaque band(s), and the heat bonding embeds the radiopaque marked band also. Placement of the marker band under metal wire can prevent the band from being separated from the catheter in the event that the wall is kinked or collapsed. If collapse or kinking of the catheter wall occurs, the braid-wire over the surface of the band collapses down over the marker band to prevent it from separating from the structure.

Figure 29:
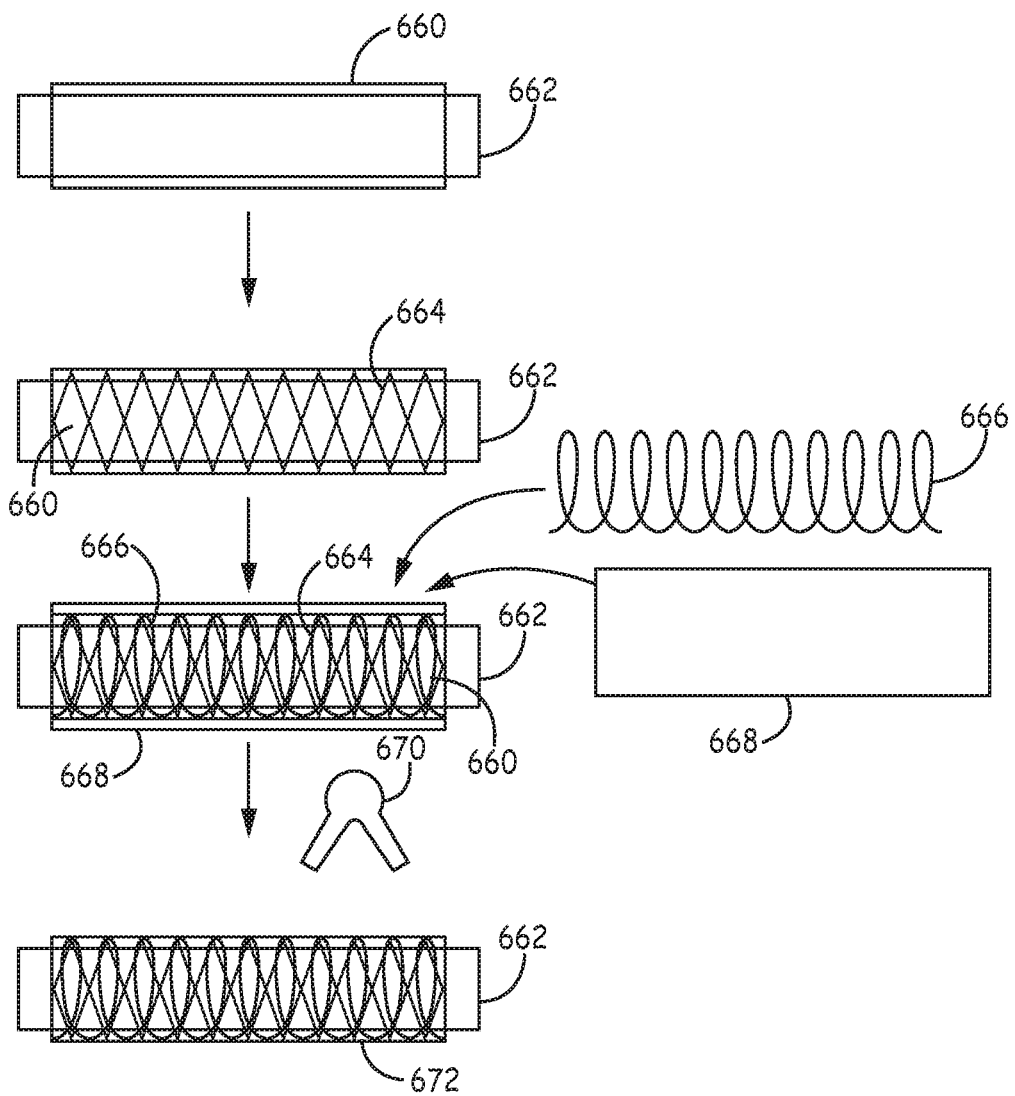
FIG. 29 is a series of side views depicting the construction of a catheter structure on a mandrel in which one or more steps are performed including application of a wire braiding, placement of a metal coil, application of a polymer over sheet and heating the polymer to embed the metal structures within the polymer.

Referring to FIG. 29, an example of a procedure for forming a section of reinforced catheter is shown. Polymer liner 660 is placed over mandrel 662. In the second sequential figure, braided wire 664 has been placed over the polymer liner, and commercial braiding equipment can be used for this step. As shown in the third figure of the series, a metal coil 666 is placed over braided wire 664 and a polymer cover 668 is placed over the metal coil 666. A heat source 670 can be used to heat shrink polymer cover 668 to complete the reinforced catheter section 672, as shown in the fourth sequential figure of FIG. 29.

Catheter Structures—Delivery Catheter with Elastic Guide Tip

In some embodiments, to facilitate delivery of medical devices to vessels along a circuitous route, a delivery catheter can be used with an expandable elastic tip. The delivery catheter comprises an elastic tip having an initial un-stretched diameters relatively small relative to a guidewire diameter. Due to the elasticity and small diameter guiding close tracking, the elastic tip can be guided along the guidewire following a circuitous route. Once the delivery catheter is in place, the lumen of the delivery catheter can provide a relatively low friction pathway for delivery of medical devices that would be more difficult to track solely over the guidewire. Because of the elasticity of the delivery catheter tip, the delivered medical device can be pushed out from the tip, which can expand to accommodate the device, to a treatment location in the vessel. The delivery catheter may or may not be removed following the delivery of the desired devices.

Figure 30:
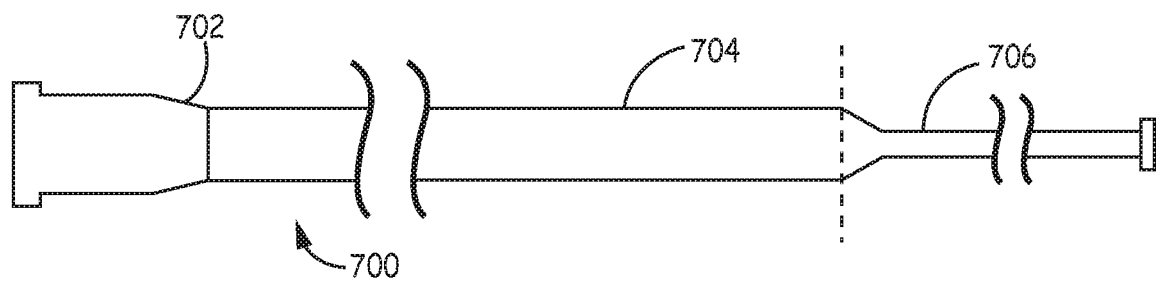
FIG. 30 is a side view of a delivery catheter having a narrow diameter elastic tip.

Referring to FIG. 30, delivery catheter 700 comprises a proximal fitting 702, tubular shaft 704 and narrow diameter elastic distal tip 706. Elastic distal tip 706 can be specified to include portions of the catheter connecting or transitioning from tubular shaft 704 to the distal tip, as shown with the dashed line in FIG. 30 since most or all of a connection/transition portion can be designed to expand to provide for the delivery of medical devices through the delivery catheter. Proximal fittings can be any suitable design, such as a conventional design, e.g., Tuohy-Borst adapter or the like, to allow for the placement of appropriate hemostatic valves or the like. Tubular shaft 704 can be designed similarly to tubular shaft 108 of FIG. 1 and can comprise metal reinforcement, such as braiding, coils or the like. Thus, the discussion of catheter materials and construction above can apply equally to tubular shaft 704 and is included here by reference without expressly repeating the language. With respect to dimensions of tubular shaft 704, the diameter can be selected to allow for passage of the largest medical device planned for delivery through the delivery catheter. Generally, tubular shaft 704 can have an outer diameter from about 1 mm to about 3.5 mm, in further embodiments from about 1.2 mm to about 3 mm, and in other embodiments from about 1.333 mm to about 2.666 mm. The length of tubular shaft 704 can be from about 30 cm to about 150 cm, in further embodiments from about 35 cm to about 130 cm and in additional embodiments from about 40 cm to about 120 cm. A person of ordinary skill in the art will recognize that additional ranges of dimensions of the tubular shaft within the explicit ranges above are contemplated and are within the present disclosure.

The elastic distal tip generally is long enough to provide its tracking function. In some embodiments, elastic distal tip 706 has a length of an approximately constant diameter section from about 5 mm to about 10 cm, in further embodiments from about 7.5 mm to about 8 cm and in other embodiments from about 1 cm to about 7 cm. The inner diameter of the distal end of elastic distal tip 706 generally can be approximately equal to the diameter of a corresponding guidewire or larger by a millimeter or less, in further embodiments, 0.75 mm or less and in some embodiments 0.5 mm or less. With respect to absolute dimensions of the inner diameter of the distal end of elastic distal tip 706, the inner diameter can be at least a factor of two smaller than the inner diameter of tubular shaft 704 and can be no more than about 2.0 mm, in further embodiments from about 0.2 mm to about 1.5 mm and in other embodiments from about 0.25 mm to about 1.25 mm. A person of ordinary skill in the art will recognize that additional ranges of elastic distal tip dimensions within the explicit ranges above are contemplated and are within the present disclosure. The elastic distal tip may have various shapes including the transition region, and as long as the tip appropriately tracks over the guidewire, the shapes are not otherwise limited. For example, the narrowest diameter portion of the elastic distal tip may be a small fraction of the total length of the elastic distal tip or a large fraction of the length of the elastic distal tip.

The materials and dimensions of the delivery catheter tip can be selected to provide for placement of a treatment structure past the delivery catheter through the expansion of the deliver catheter expandable tip. The expansion of the tip may or may not expand the polymer of tip beyond its elastic limit. If stretched beyond the polymer's elastic limit, the tip does not relax back to its original shape once the stresses are removed, but once in position, the tip's original narrow configuration is no longer used to guide the tip. Generally, the elastic tip can stretch to at least 1.5 times the initial inner diameter, in further embodiments at least about 2 times, and in other embodiments at least about 2.5 times the initial inner diameter at the distal end of the distal tip. A plurality of therapeutic devices can be sequentially delivered through the delivery catheter, and previously delivered devices may or may not be removed prior to delivery of additional devices depending on their intended use. At an appropriate time on the procedure, the delivery catheter can be removed, which may be prior to the completion of therapeutic treatments. Various elastomeric polymers can be used to form elastic distal tip 706. Suitable elastomers include, for example, rubber, synthetic rubbers (polyisoprene), polybutadiene, styrene-butadiene copolymer, nitrile rubber, silicone rubber, polyether block amides, vinylidene fluoride, polyurethane elastomers (such as Estane®, Pellethane®, Tecothane®, Tecoflex® and Carbothene™ all from Lubrizol), polychronoprene (such as Neoprene™ from PuPont) and the like.

Figure 31:
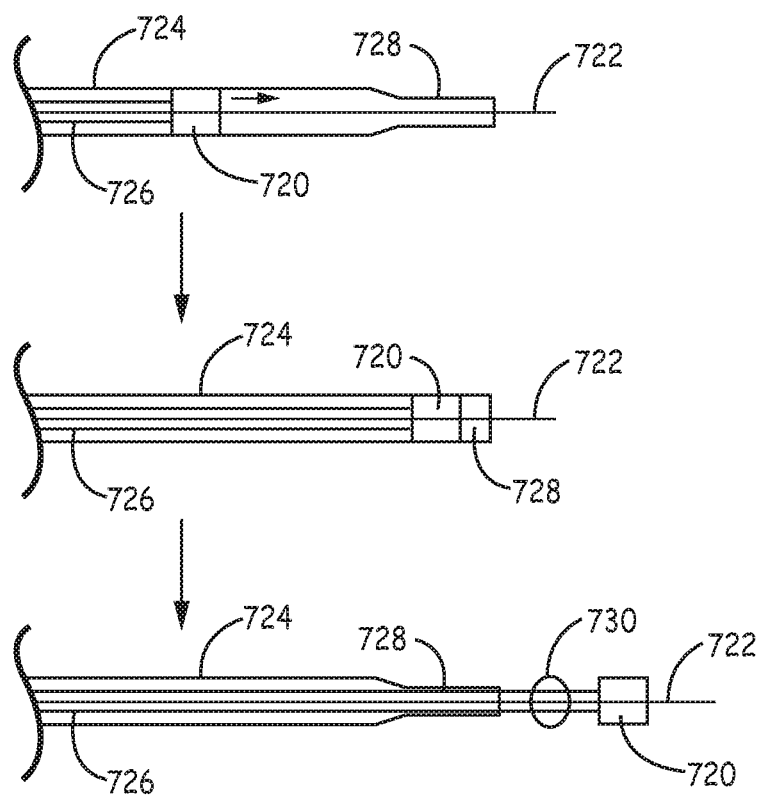
FIG. 31 depicts a series a fragmentary side views with a medical device progressively delivered with assistance of a delivery catheter of FIG. 30 in which the medical device for delivery a) is initially depicted in the proximal section of the catheter, b) is expanding the elastic tip for delivery past the elastic tip, and c) is located on the distal side of the elastic tip.

Delivery of a therapeutic device with the delivery catheter is shown schematically in FIG. 31. In the first view, first medical device 720 is delivered over guidewire 722 through delivery catheter 724, push structure 726, such as a catheter can be used to advance first medical device 720. Downward arrows indicate later stages of the procedure. In the second view, first medical device 720 is being pushed through elastic distal tip 728, which is shown in an extended state to provide for the passage of first medical device 720. Referring to the last view in FIG. 31, first medical device 720 and a second medical device 730 are shown advanced past elastic distal tip 728 of delivery catheter 724. Delivery catheter 724 may or may not be removed prior to performing additional steps of the procedure.

Treatment Systems

The suction system described herein can be used effectively to remove blood clots from the vasculature, including the vasculature of the brain to treat acute stroke conditions. In particular, the narrow tip catheter of the '313 application have performed well in human clinical trials to restore blood flow in persons with an acute embolic stroke with good patient performance. The device described herein may be expected to provide even better suction while maintaining access capability into vessels challenging to navigate. Nevertheless, for some acute stoke conditions or other embolic events, it can be desirable to use the suction catheter systems described herein with other medical tools for performing the therapy.

Figure 32:
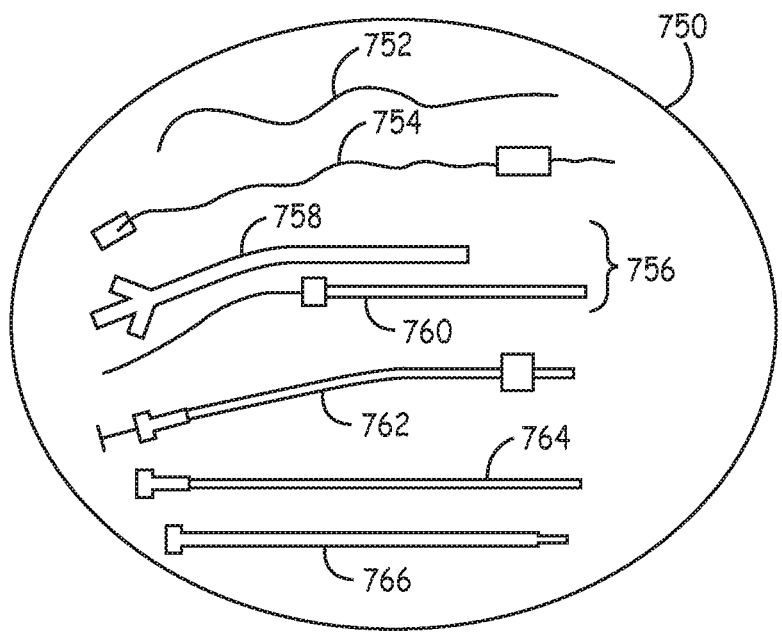
FIG. 32 is a schematic depiction of a collection of medical devices that can be used together or in selected sub-combinations for selected percutaneous procedures in bodily vessels including a suction system as described herein and a delivery catheter as described herein.

Referring to FIG. 32, a treatment system 750 is shown comprising a guidewire 752, embolic protection system 754, suction system 756, shown with guide catheter 758 and suction extension 760 separated, a percutaneous medical device 762, microcatheter 764 and delivery catheter 766. Not all embodiments of medical systems may have all of these components, and some medical system embodiments may have multiple components of each type, such as multiple distinct percutaneous medical devices. Guidewires suitable for use in tortuous bodily vessels are described in copending published U.S. patent application Ser. No. 2016/0199620 A1 to Pokorney et al., entitled "Medical Guidewires for Tortuous Vessels," incorporated herein by reference. In some embodiments, embolic protection system 754 can comprise a guide structure to provide for delivery of the device as a guide wire, and for these systems a separate guidewire may or may not be used. Suction system 756 embodiments are described in detail herein, and the various embodiments described herein can be adapted for use with the medical systems as well as stand alone devices. If desired for particularly challenging device delivery, the medical system can include a delivery catheter 766, as described herein.

Embolic protection devices with small filter lateral extent and designed for suitable manipulations to facilitate delivery in vessels have been developed that are suitable for use in the medical systems described herein. See, for example, U.S. Pat. No. 7,879,062B2 to Galdonik et al., entitled "Fiber Based Embolism Protection Device," and U.S. Pat. No. 8,092,483B2 to Galdonik et al., entitled "Steerable Device Having a Corewire Within a Tube and Combination with a Functional Medical Component," both of which are incorporated herein by reference. FiberNet® embolic protection devices based on the technology in these patents are commercially available from Medtronic Inc. Additional fiber-based filter devices particularly designed for delivery into tortuous vessels are described in U.S. Pat. No. 8,814,892B2 to Galdonik et al. (hereinafter the '892 patent), entitled "Embolectomy Devices and Methods of Treatment for Acute Ischemic Stroke Condition," incorporated herein by reference. The '892 patent describes the use of the filter device as a clot engagement tool for use with an aspiration catheter. The '892 patent also envisions the use of supplementary structures to facilitate engagement of the clot. The use of supplementary structures are also contemplated in procedures described herein.

Microcatheters have been designed to allow for access to small blood vessels, such as cerebral blood vessels, and cerebral microcatheters are available commercially, e.g., Prowler Select™ (Cordis Neurovascular Inc.) and Spinnaker Elite™ (Boston Scientific Co.). Of course the term microcatheter can cover a range of devices, and the present discussion can focus on catheters useful for the procedures described herein. In some embodiments, microcatheters can comprise a distal section that is narrower than a proximal section. However, in further embodiments, a microcatheter can have an approximately constant diameter along its length to facilitate delivery of other devices over the microcatheter. A narrow distal diameter allows for the catheter to navigate the tortuous vessels of the brain. The distal section can be highly flexible enough to navigate the vessels, but resilient enough to resist kinking. A microcatheter comprises at least one lumen. The microcatheter can then be used to deliver other treatment devices, aspiration, therapeutic agents, or other means of treating a condition. While microcatheters can have a selected size, in some embodiments, the microcatheters can have a distal outer diameter from about 1.0 Fr to about 3.5 Fr and in further embodiments from about 1.5 Fr to about 3 Fr, and a length from about 30 cm to about 200 cm and in further embodiments from about 45 cm to about 150 cm. A person of ordinary skill in the art will recognize that additional size ranges within the explicit ranges above are contemplated and are within the present disclosure.

With respect to percutaneous medical devices 762, suitable devices include, for example, angioplasty balloons, stent delivery devices, atherectomy devices, such as stent retrievers, and the like. Stents may be, for example, balloon extendable, self-extendable or extendable using any other reasonable mechanism. Balloon extendable stents can be crimped to the balloon for delivery. Some balloon-stent structures are described further, for example, in U.S. Pat. No. 6,106,530, entitled "Stent Delivery Device;" U.S. Pat. No. 6,364,894, entitled "Method of Making an Angioplasty Balloon Catheter;" and U.S. Pat. No. 6,156,005, entitled "Ballon [sic] Catheter For Stent Implantation," each of which are incorporated herein by reference. Self-expanding stents are described further in U.S. Pat. No. 8,764,813 to Jantzen et al., entitled "Gradually Self-Expanding Stent" and U.S. Pat. No. 8,419,786 to Cottone, Jr. et al., entitled "Self-Expanding Stent," both of which are incorporated herein by reference. Stent retrievers are described, for example, in U.S. Pat. No. 8,795,305 to Martin et al., entitled "Retrieval Systems and Methods for Use Thereof," incorporated herein by reference.

Procedures Making Use of Treatment Systems

As indicated above, the medical systems comprising a suction system described herein can be used with the suction system as stand alone treatment device, perhaps with a guidewire and/or other delivery support devices, or used with supplemental medical devices for treatment of ischemic vessel blockage. In particular, in some embodiments, the suction system is used with an embolic protection device, and in additional embodiments, some form of stent, balloon, athetectomy device or the like may also be used. In any case, a guidewire is generally used to provide access to the treatment site. The guide catheter portion of the suction device may or may not be positioned prior to the introduction of the suction extension. The structures of the particular components are described in detail above, and are not repeated so that this section can focus on the use of the devices.

Figure 33:
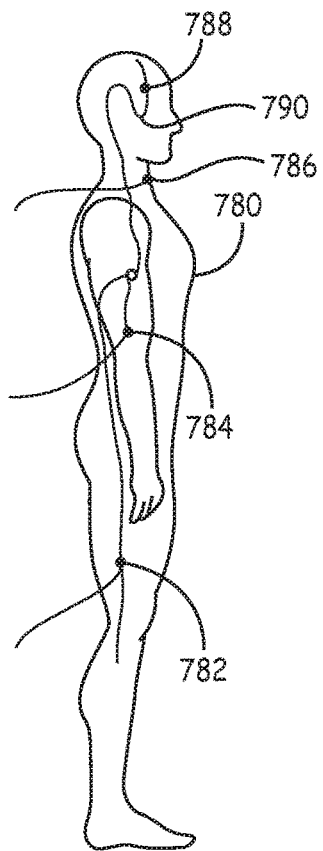
FIG. 33 is a schematic depiction of a human patient with alternative access approaches for directing catheters into the blood vessels of the brain.
Figure 34:
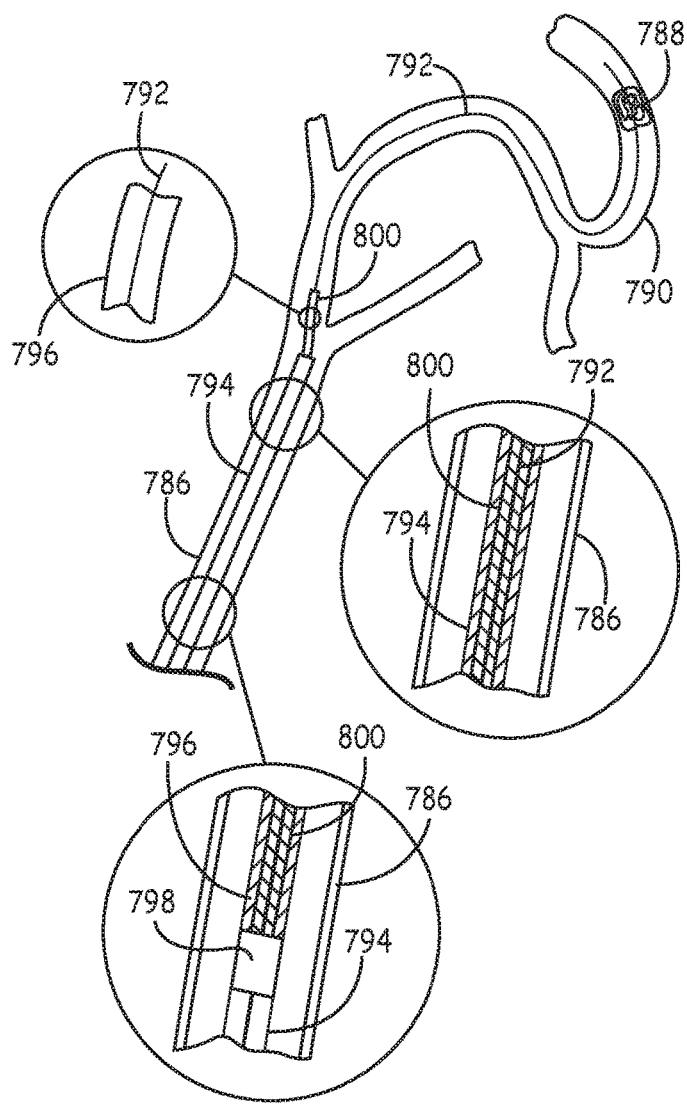
FIG. 34 is a view within a branched blood vessel section showing the delivery of medical devices along a guidewire from a guide catheter to a clot. Inserts show expanded views of two internal sections of the guide catheter.
Figure 35:
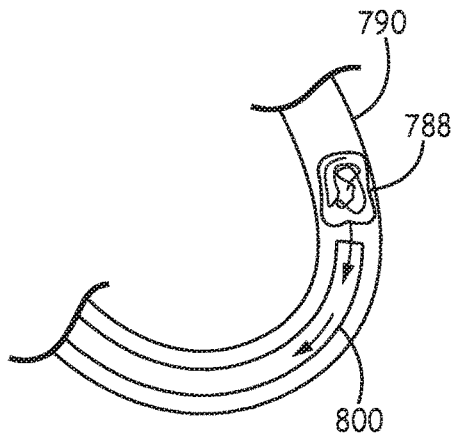
FIG. 35 is a schematic view in a section of blood vessel of a suction system being used to remove a clot.

For the treatment of an acute aschemic stroke condition, referring to FIG. 33, a patient 780 is shown with three alternative access points into the vasculature, femoral artery 782, artery in the arm 784 or carotid artery in the neck 786. Regardless of the access point, the catheter and associated devices are guided to the left or right carotid artery to reach a clot 788 in a cerebral artery 790 of the brain. Referring to the schematic view in FIG. 34, clot 788 is shown in cerebral artery 790 with a guidewire 792 positioned with its distal tip past the clot. Guide catheter 794 is positioned over the guidewire within the carotid artery 786. Suction extension 796 with proximal portion 798 within guide catheter 794 and suction tip 800 extending from guide catheter 794 over guidewire 792. Referring to FIG. 35, the suction tip can be advanced over the guidewire to a position near clot 788. Suction can be applied as shown with the flow arrows in the figure. Guidewire 792 may or may not be removed before suction is applied. Suction catheters have successfully removed clots responsible for ischemic stroke without further medical devices in the intervention. However, for more difficult clots, additional medical devices can be used as described in the following.

Figure 36:
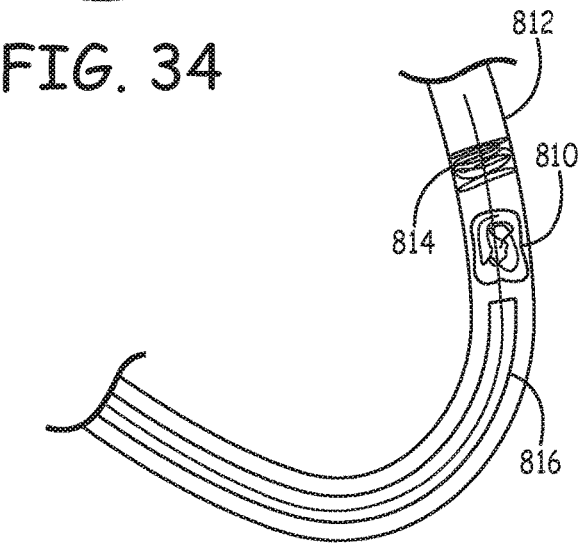
FIG. 36 is a schematic view in a section of blood vessel with a suction system positioned upstream from a clot and a fiber based filter deployed downstream from the clot.
Figure 37:
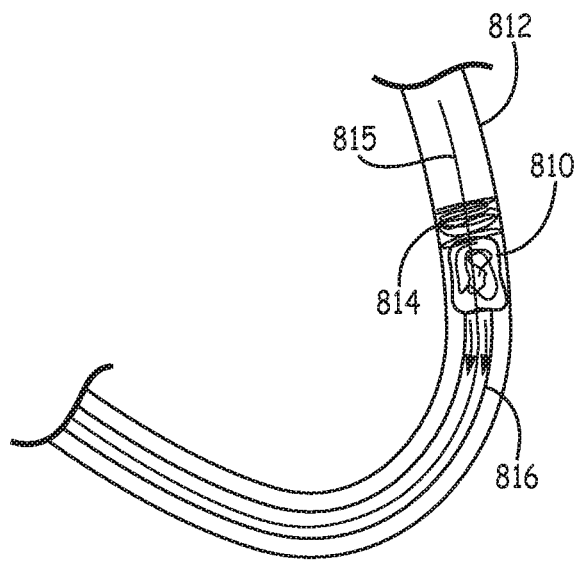
FIG. 37 is a schematic view of the section of blood vessel of FIG. 36 with the fiber based filter being drawn toward the suction tip to draw the clot to the tip for facilitating removal of the clot.

Referring to FIGS. 36 and 37, the use of a fiber-based filter device is shown in use along with the aspiration system. As shown in FIG. 36, clot 810 is shown in cerebral artery 812 with a deployed fiber-based filter 814 supported on a suction tip 816 positioned with the filter deployed past the clot. Fiber-based filter 814 can have fiber elements extending to the wall of the vessel, cerebral artery 812. Suction tip 816 can be positioned just proximal to the clot, and the remaining portions of the suction system are not shown in this view. Referring to FIG. 37, fiber-based filter 814 can be pulled toward suction tip 816 with suction being applied to facilitate removal of clot 810. Clot 810 can be broken up and removed by suction, and/or all or a portion of clot 810 can be pulled into suction tip 816 optionally along with all or part of the fiber-based filter, and/or all or a portion of clot 810 can be held to the opening of suction tip 816 with the fiber-based filter holding the clot. In any case, once the clot is appropriately stabilized, the devices and any clot still within the vessel or catheter can be removed from the patient.

Figure 38:
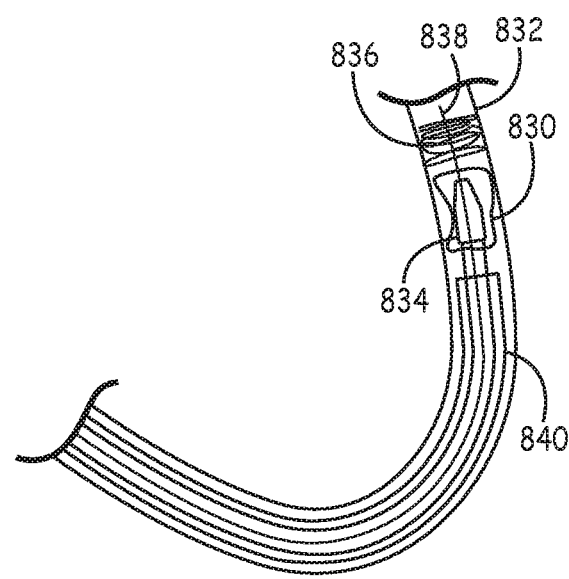
FIG. 38 is a schematic view of a section of blood vessel with a suction system positioned upstream from a clot, a fiber based filter deployed downstream from the clot and another medical device positioned at the clot.
Figure 39:
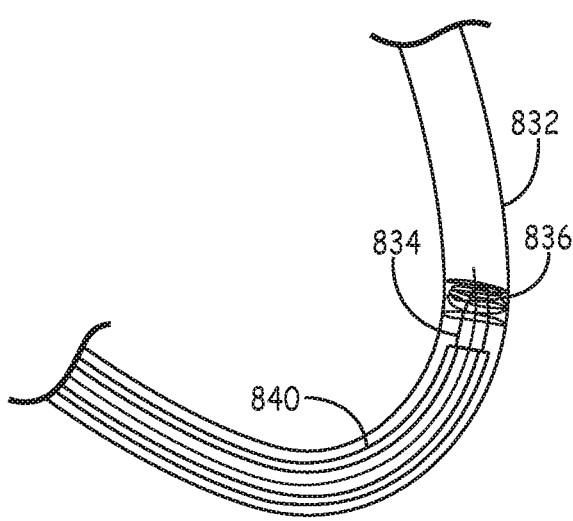
FIG. 39 is a schematic view of the section of blood vessel of FIG. 38 with the various medical devices being used in concert for the removal of the clot.

The further use of an additional medical device to facilitate clot removal is shown in FIGS. 38 and 39. As shown in FIG. 38, clot 830 is shown in cerebral artery 832 with a medical device 834 positioned at the clot and deployed fiber-based filter 836 supported on a guidewire 838 positioned with the filter deployed past the clot. Suitable medical devices include, for example, angioplasty balloons, stents delivery systems, stent retrievers, other atherectomy devices and the like, and these are described further above. The selected medical device is deployed generally with protection from the deployed fiber-based filter and optionally with suction. Once the clot is treated with the medical device, the recovery of the remaining portions of the clot and the medical devices can be removed as shown in FIG. 39, similarly to the process shown in FIG. 37. In particular, the medical device can be removed, although portions such as a stent may be left behind, and the removal can precede or be done in conjunction with removal of the filter and/or remaining fragments of clot. All or a portion of clot 830, if not already broken up and removed with suction can be pulled into suction tip 840 optionally along with all or part of the fiber-based filter, and/or all or a portion of clot 810 can be held to the opening of suction tip 840 with the fiber-based filter holding the clot. Again, once the clot is appropriately stabilized, the devices and any clot still within the vessel or catheter can be removed from the patient. The use of a plurality of additional medical devices can be performed through extension of the procedure outlined above to repeat steps involving the additional medical device.

The suction system is generally appropriately sterilized, such as with e-beam or gas sterilization. The suction system can be packaged together or separately in a sealed package, such as plastic packages known in the art. The package will be appropriately labeled, generally according to FDA or other regulatory agency regulations. The aspiration system can be packages with other components, such as a guidewire, filter device, and/or other medical device. The packaged system generally is sold with detailed instructions for use according to regulatory requirements.

Bench Testing and Calculations

To evaluate the performance of the suction tip with a substantial portion of the aspiration lumen provided by the guide catheter both bench testing and calculations were performed. Both the bench testing and calculation confirm the excellent performance of the suction systems described herein with surprising strong suction obtained with the suction tip. With respect to calculation, both fluid dynamic calculations and modeling were performed with consistent results.

Figure 40:
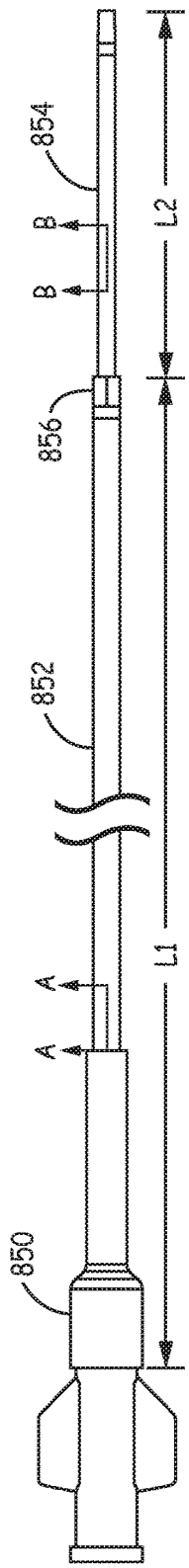
FIG. 40 is a side view of a prototype suction system with a fixed suction tip.
Figure 41:
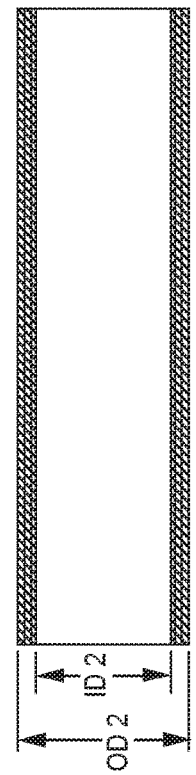
FIG. 41 is a fragmentary sectional view of the guide catheter of the suction system of FIG. 40 with the section taken along line A-A of FIG. 40.
Figure 42:
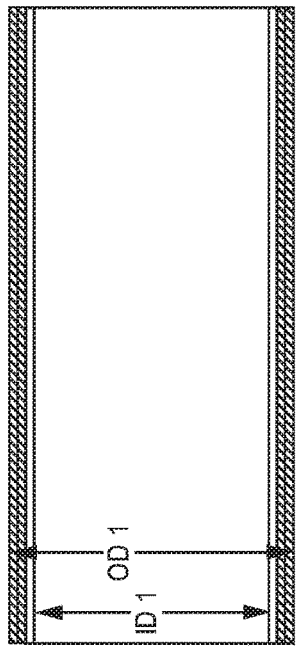
FIG. 42 is a fragmentary sectional view of the suction tip of the suction system of FIG. 40 with the section taken along line B-B of FIG. 40.

Bench testing was performed with seven suction catheters: two prototype nozzle/suction system along with two MIVI Neuroscience, Inc. commercial suction catheters with a reduced diameter distal portion, and three Penumbra, Inc. suction catheters with reduced diameter distal portions. The prototype suction systems was formed without the ability to slide the suction tip position to simplify the construction, but they were based on a guide catheter used for the corresponding component of the system. FIG. 40 shows one of the prototypes, and cross sections are shown in FIGS. 41 and 42. The prototype has a standard catheter fitting (Luer Lock) 850 attached at its proximal end, a catheter shaft 852, suction tip 854 and a sealed connection 856 with a 2 mm overlap. Catheter shaft 852 including a section of the shaft extending into a designated portion of the catheter fitting 850 has a length of 31.777 inches. Catheter shaft 852 has a constant diameter (FIG. 41) with an inner diameter (ID1) of 0.90 inches and an outer diameter of 0.108 inches (2.74 mm or 8.2 Fr). Suction tip (FIG. 42) had a length of 7.8 inches, an inner diameter (ID2) of 0.054 inch and an outer diameter (OD2) of 0.065 inch (1.65 mm or 5.0 Fr). The suction tip overlapped 2 mm with catheter shaft 852, and the total length was about 1 m (39.4 inches). A second prototype was the same except for having a longer guide catheter (1 m) and a longer suction extension (0.3 m).

Figure 43:
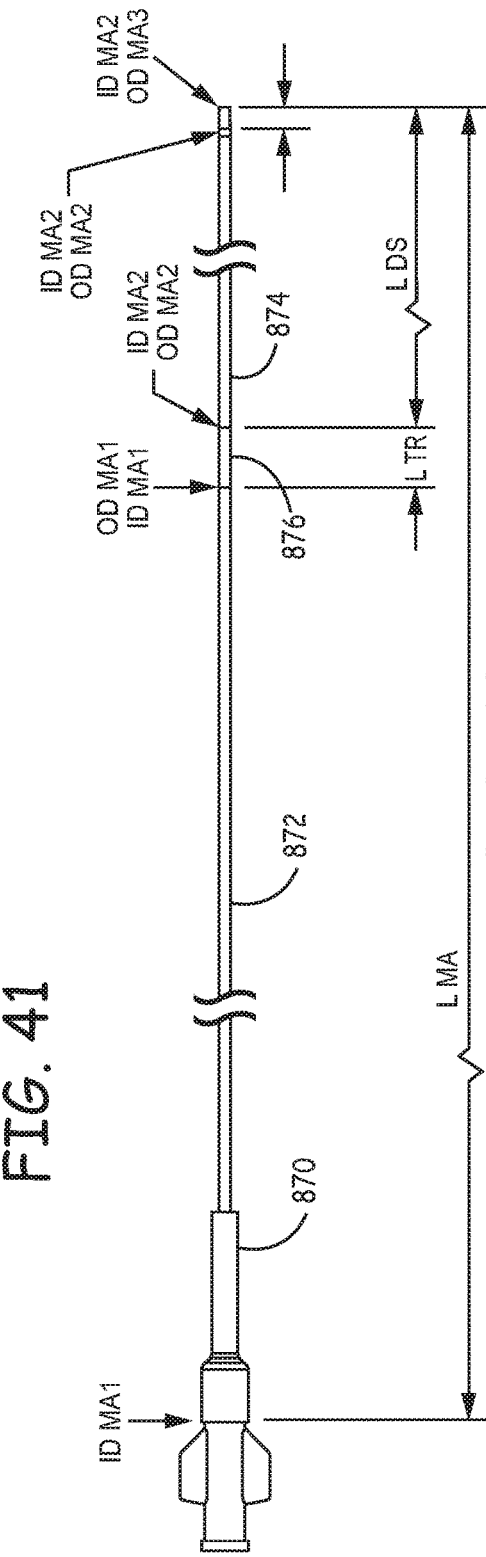
FIG. 43 is a side view of a MI-AXUS commercial catheter used for comparative measurements of suction performance.

For comparison, bench testing was also performed with two sizes of MI-AXUS™ 6 suction catheter (MIVI Neuroscience, Inc.), and 5MAX, 5MAX ACE™ and 3MAX commercial catheters (Penumbra, Inc.). The Mi-Axus™ 6 catheter is shown in FIG. 43 and comprises a proximal fitting 870, proximal shaft 872, distal shaft 874 and transition region 876. Proximal shaft 872 (including a section of proximal shaft extending into the proximal fitting as marked), distal shaft 874, transition region 876 has a total length L MA of 50.906 inches (1.28 m). Transition region 876 has a length L TR of 0.39 inches, and distal shaft 874 has a length L DS of 9.96 inches. Proximal shaft 872 has an inner diameter (ID MA1) of 0.064 inch and an outer diameter (OD MA1) of 0.075 inch, and distal shaft 874 has an inner diameter (ID MA2) of 0.054 inch and an outer diameter (OD MA2) of 0.065 inch except for an outer diameter taper (OD MA3) to 0.058 inch over the last 0.12 inches of length of the catheter. A second MI-AXUS 6 catheter had a shorter total length of about 1.10 m. The properties of the seven catheters that were bench tested is summarized in Table 1.

TABLE 1

| Catheter | Proximal Inner Diameter (Fr) | Distal Inner Diameter (Fr) | Total Length (m) | Distal Tip Length (m) |
|---|---|---|---|---|
| Prototype 1 | 6.705 | 4.11 | 0.98 | 0.18 |
| Prototype 2 | 6.705 | 4.11 | 1.32 | 0.30 |
| MI-AXUS 6 (1) | 4.80 | 4.30 | 1.28 | 0.27 (1 cm transition) |
| MI-AXUS 6 (2) | 4.80 | 3.90 | 1.10 | 0.27 (1 cm transition) |
| 5MAX | 4.89 | 4.11 | 1.32 | |
| 5MAX ACE | 5.19 | 4.56 | 1.32 | |
| 3MAX | 3.27 | 2.67 | 1.53 | |

Figure 44:
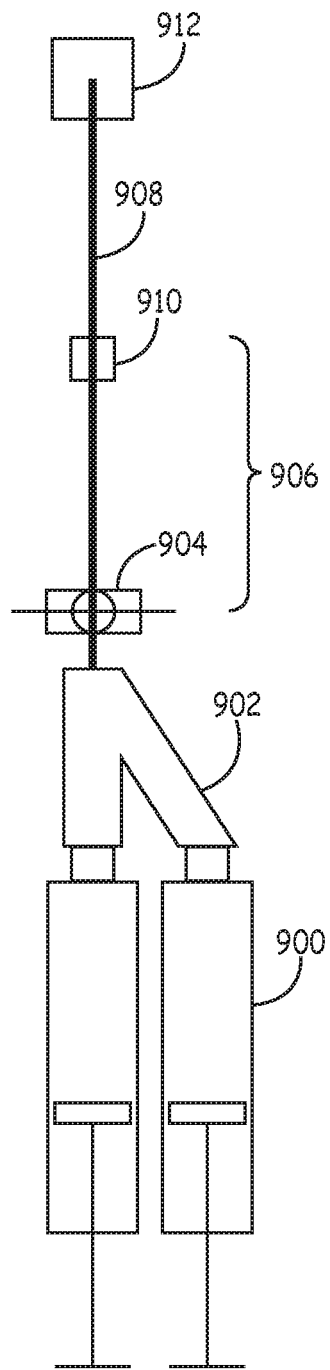
FIG. 44 is a schematic view of a catheter suction test set up used to test the suction system prototype and comparative catheters.

To conduct the bench testing, two 30 cc syringes were used in parallel with a closed stopcock. A schematic diagram of the test set up is shown in FIG. 44. A shown, two 300 cc syringes 900 are connected to a Y-adapter 1902, which connects to a 2-way stopcock 1904. Stopcock 1904 is connected to a short length of tubing 1906 that has a luer lock fitting element that then is connected to the corresponding Luer lock fitting element on the catheter 1908 to form connected fitting 1910. The distal end of the catheter is in a water reservoir 1912. The syringes were fully retracted and locked in place. A timer was set and the valve was opened for a selected amount of time. The extracted water was then weighed to obtain an accurate reading of the amount of water. This configuration was measured to produce a maximum gauge pressure of 89 kPa and an average of roughly 78 kPa. The fluid transmission results are presented in Table 2.

TABLE 2

| Catheter | Flow Rate Measured (mL/s) | Flow Rate ANSYS (mL/s) | Flow Rate (Pipeflow)(mL/s) |
|---|---|---|---|
| Prototype 1 | 5.569 | 5.801 | 10.65 |
| Prototype 2 | 5.280 | 4.155 | 7.319 |
| MI-AXUS 6 (1) | 4.550 | 2.872 | 2.648 |
| MI-AXUS 6 (2) | 3.680 | 2.392 | 2.927 |
| 5MAX | 4.036 | 2.880 | 2.701 |
| 5MAX ACE | 4.877 | 3.180 | 3.529 |
| 3MAX | 1.342 | 0.406 | 0.463 |

The prototype catheters had significantly improved suction performance relative to all of the other catheters. Thus, based on the flow rate measurements, a flow rate of at least 5 mL/s and in some embodiments at least about 5.25 mL/s can be established with the catheter systems based on a suction pressure of −78 kPa. A person of ordinary skill in the art will recognize that additional ranges of flow rate within the explicit ranges above are contemplated and are within the present disclosure. For comparison, simulations were performed and fluid dynamics calculations were also performed. In general, the calculated values were not quantitative, but reasonably indicated trends. The ANSYS simulations were somewhat more predictive of the trends than the Pipeflow calculations, such as the correct ordering of the two Mi-AXUS flow rates.

Analytical fluid dynamic calculations were performed using a web based "Pipe Flow Calculator." The analytical calculations were available on htp://www.pipeflowcalculations.net/pressuredrop.xhtmp. The following settings were used for calculations: 1060 kg/m³, dynamic viscosity 3.3 centipoise, p1 1 atmosphere, and delta p–75 kPa. To perform these calculations, an average inner diameter had to be input. Calculated flow rates for the catheters used in the bench testing can be found in Table 2.

The simulation results were performed with ANSYS CFX R16.1 software (ANSYS Inc.). To perform the simulations, some assumptions were tested and determined to yield appropriate results with negligible effect on the results. A Steady State solution was determined, neglecting the impact of unsteady and turbulent effects on the flow as in the "flow regime" internal to the catheter is also well within the theoretical limit for "laminar" or steady flow. The fluid directly outside the walls of the catheter was neglected, and it was sufficient to simulate a fluid region of 5 cm forward of the distal tip. The tip was modeled as being of constant diameter, which greatly increases the regularity with which the simulation determined fluid properties at each point while reducing computational time, and while also introducing negligible, conservative inaccuracy. For both cases, the simulation assumed to have "converged" when the "residuals", i.e. the unsolved leftovers from the thousands of approximated differential equations, drop below a certain, specified threshold. This threshold, in standard practice, is $1.0 \times 10^{-4}$. For these simulations, the threshold was set to be $1.0 \times 10^{-6}$, which required more computational time, and produced more accurate results. A maximum number of iterations, i.e., the number of times the simulation refines its calculations, is in standard practice 100.

The fluid region is set to be a homogenous fluid, of density 1060 kg/m³, dynamic viscosity of 3.3 centipoise, and temperature equal 20 degrees C. with no heat transfer. Two simulations were done for each geometric configuration. To determine volumetric flow rate in cc/s, a 75 kPa pressure difference was then applied as a boundary condition between the proximal and distal ends of the fluid region. For determining the pressure loss, a mass flow rate was specified across the proximal and distal ends of the fluid region. Simulated flow rates for the catheters used in the bench testing are found in Table 2.

In the spirit of evaluating additional prototype performance using simulation and calculations, additional evaluations were performed with a range of catheter dimensions using both ANSYS and the pipe flow calculator. The catheter parameters are found in Table 3 and the results are presented in Table 4.

TABLE 3

| Model Catheter | Proximal Inner Diameter (Fr) | Distal Inner Diameter (Fr) | Total Length (m) | Distal Tip Length (m) |
|---|---|---|---|---|
| Straight 1 | 6.00 | 6.00 | 1.20 | — |
| Straight 2 | 5.00 | 5.00 | 1.20 | — |
| Straight 3 | 2.10 | 2.10 | 1.20 | — |
| Straight 4 | 4.88 | 4.88 | 1.32 | — |
| Straight 5 | 5.18 | 5.18 | 1.32 | — |
| Extended Tip 1 | 8.00 | 6.00 | 1.20 | 0.20 |
| Extended Tip 2 | 4.00 | 2.10 | 1.20 | 0.20 |
| Extended Tip 3 | 6.81 | 3.90 | 1.20 | 0.60 |
| Extended Tip 4 | 6.81 | 3.90 | 1.20 | 1.00 |
| Extended Tip 5 | 6.705 | 4.70 | 1.32 | 0.30 |
| Extended Tip 6 | 6.705 | 4.60 | 1.32 | 0.30 |
| Extended Tip 7 | 6.705 | 4.50 | 1.32 | 0.30 |
| Extended Tip 8 | 6.705 | 4.25 | 1.32 | 0.30 |
| Extended Tip 9 | 6.705 | 4.11 | 1.20 | 0.30 |
| Extended Tip 10 | 6.705 | 4.88 | 1.32 | 0.30 |
| Extended Tip 11 | 6.705 | 2.10 | 1.50 | 0.60 |

TABLE 4

| Catheter | Pressure Drop ANSYS (kPa) | Flow Rate ANSYS (mL/s) | Flow Rate (Pipeflow)(mL/s) |
|---|---|---|---|
| Straight 1 | — | 3.360 | 7.437 |
| Straight 2 | — | — | 3.590 |
| Straight 3 | — | 0.008 | 0.112 |
| Straight 4 | 88.05 | — | 2.959 |
| Straight 5 | 69.31 | — | 3.756 |
| Extended Tip 1 | — | 8.030 | 13.26 |
| Extended Tip 2 | — | 0.044 | 1.060 |
| Extended Tip 3 | — | 4.084 | 4.772 |
| Extended Tip 4 | — | 3.162 | 2.112 |
| Extended Tip 5 | 41.77 | 5.682 | 7.960 |
| Extended Tip 6 | 43.83 | 5.460 | 7.858 |
| Extended Tip 7 | 46.14 | 5.212 | 7.714 |
| Extended Tip 8 | 53.24 | 4.533 | 7.463 |
| Extended Tip 9 | — | 5.387 | 7.739 |
| Extended Tip 10 | 38.53 | 6.147 | 8.218 |
| Extended Tip 11 | — | 0.311 | 2.561 |

As demonstrated by these experiments and calculations, the suction catheter systems described herein can achieve improve suction through a narrow tip that can be used to access remote blood vessels.

The embodiments above are intended to be illustrative and not limiting. Additional embodiments are within the claims. In addition, although the present invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein.

What is claimed is:

1. A suction catheter system comprising:
a guide catheter comprising a tubular shaft with a central lumen having an inner diameter, a proximal end and a distal opening, and a proximal section operably connected with the proximal end of the tubular shaft and having fittings that connect to a suction device; and
a suction extension comprising a proximal portion, a suction tip comprising a distal opening and extending from the proximal portion in a distal direction, and a control structure connecting the proximal portion with the proximal section of the guide catheter, the suction tip having a distal inner diameter that is from about 20 percent to about 90 percent of the central lumen inner diameter, wherein the proximal portion is configured to slide within the central lumen of the tubular shaft to change the relative position of the proximal portion within the central lumen and provide for at least a portion of the narrow diameter suction extension to extend outward from the distal opening of the tubular shaft at appropriate configurations of the proximal portion, wherein an effective seal is formed by a tight fit between the proximal portion and the central lumen of the guide catheter and wherein the proximal portion comprises a seal element having a lateral extent to form the effective seal for continuous engagement from about 5 millimeters (mm) to about 25 centimeters (cm), wherein a suction lumen is formed extending from the fitting configured to connect to the suction device through a portion of the central lumen, the proximal portion and the suction tip to a distal opening.

2. The suction catheter system of claim 1 wherein the proximal portion of the suction extension further comprises a balloon mounted on its exterior and a tube connected to the interior of the balloon forming a balloon lumen, the tube extending through the central lumen of the guide catheter to a fitting of the proximal section.

3. The suction catheter system of claim 1 wherein the central lumen of the guide catheter comprises a stop that limits the proximal portion of the suction extension within the central lumen of the guide catheter.

4. The suction catheter system of claim 1 wherein the guide catheter has an outer diameter ranging from about 6 Fr to about 10 Fr.

5. The suction catheter system of claim 1 wherein the suction tip has an inner diameter from about 40 percent to about 80 percent of the central lumen inner diameter.

6. The suction catheter system of claim 1 wherein the shaft of the guide catheter has a length from about 0.5 m to about 1.8 m and the suction tip has a length from about 5 cm to about 50 cm, and wherein the tubular shaft has a single lumen over its entire length.

7. The suction catheter system of claim 1 wherein the suction tip comprises a plurality of segments each having a constant diameter along the particular segment with a distal segment having a smaller inner diameter than a more proximal segment.

8. The suction catheter system of claim 1 wherein the suction tip has a distal end and a curve in an unstrained configuration at the distal end.

9. The suction catheter system of claim 1 wherein a flow rate of at least about 5 mL/s is established when an aspiration gauge pressure of −78 kPa is established.

10. The suction catheter system of claim 1 wherein the suction extension is removable through the proximal end of the guide catheter.

11. The suction catheter system of claim 1 wherein a clearance within a specified tolerance is provided between the seal element and the inner surface of the guide catheter.

12. The suction catheter of claim 1 wherein the proximal portion comprises a seal element having a lateral extent to form the effective seal for continuous engagement from about 8 mm to about 18 cm.

13. A method for performing a thrombectomy procedure with the suction catheter system of claim 1, the method comprising:
applying suction through the suction lumen of the suction catheter system positioned with the guide catheter extending into a vessel of a patient in a percutaneous configuration, to draw fluid into the distal opening of the suction tip to remove thrombus from the vessel.

14. The method of claim 13 further comprising positioning the guide catheter to extend into a carotid artery with the suction tip extending into a cerebral artery.

15. The method of claim 13 further comprising deploying a fiber based filter in the vessel distal to a clot, and drawing the fiber based filter in the proximal direction while suction is applied.

16. The method of claim 15 further comprising deploying a further medical device at the location of thrombus to disrupt the thrombus while the fiber based filter is deployed.

17. A method for performing a medical procedure in a bodily vessel using a suction catheter system comprising a guide catheter and a suction extension slidably engaged with the guide catheter, the suction extension comprising a proximal portion configured to remain in a central lumen of the guide catheter wherein the proximal portion comprises a seal element having a lateral extent to form the effective seal for continuous engagement from about 5 millimeters (mm) to about 25 centimeters (cm), and a suction tip extending in a distal direction from the proximal portion, wherein a suction lumen is formed extending from the suction tip to a fitting connected at a proximal portion of the guide catheter, the method comprising:
tracking the suction tip to a desired location within a vessel by sliding the suction extension relative to the guide catheter; and
applying suction at the fittings connected to the guide catheter at the proximal portion of the guide catheter through the suction lumen that extends to the proximal end of the guide catheter.

18. The method of claim 15 wherein the tracking is performed by directing the suction tip over a guidewire, wherein the blood vessel is a cerebral artery, and wherein the proximal portion has a lateral extent from about 5 mm to about 25 cm.

19. The method of claim 15 further comprising deploying a fiber based filter extending in a distal direction from the suction tip.

20. The method of claim 18 wherein the guidewire is prepositioned with a distal tip past a target location for placement of the suction tip.

21. The method of claim 19 wherein the filter is moved toward the suction tip while suction is applied.

22. The method of claim 19 wherein the filter comprises fibers extending to the vessel wall.

23. The method of claim 19 further comprising using an atherectomy device while the filter is deployed.

* * * * *